United States Patent
Mikolajczyk et al.

(10) Patent No.: US 10,527,611 B2
(45) Date of Patent: Jan. 7, 2020

(54) DEVICES AND METHODS OF CELL CAPTURE AND ANALYSIS

(71) Applicant: BIOCEPT, INC., San Diego, CA (US)

(72) Inventors: Stephen Mikolajczyk, San Diego, CA (US); Tony Pircher, San Diego, CA (US); Pavel Tsinberg, Carlsbad, CA (US); Farideh Z. Bischoff, Sugar Land, TX (US)

(73) Assignee: Biocept, Inc., San Diego, CA (US)

( * ) Notice: Subject to any disclaimer, the term of this patent is extended or adjusted under 35 U.S.C. 154(b) by 304 days.

(21) Appl. No.: 14/812,498

(22) Filed: Jul. 29, 2015

(65) Prior Publication Data

US 2016/0025720 A1 Jan. 28, 2016

Related U.S. Application Data

(62) Division of application No. 12/730,738, filed on Mar. 24, 2010, now Pat. No. 9,128,082.

(Continued)

(51) Int. Cl.
*G01N 33/536* (2006.01)
*G01N 33/543* (2006.01)
(Continued)

(52) U.S. Cl.
CPC ..... *G01N 33/54306* (2013.01); *G01N 33/536* (2013.01); *G01N 33/56966* (2013.01); *G01N 33/56972* (2013.01); *G01N 33/57492* (2013.01)

(58) Field of Classification Search
CPC ........... G01N 33/54306; G01N 33/536; G01N 33/56966; G01N 33/57492
See application file for complete search history.

(56) References Cited

U.S. PATENT DOCUMENTS

| | | | |
|---|---|---|---|
| 6,265,229 B1 * | 7/2001 | Fodstad | G01N 33/54333 422/504 |
| 6,368,871 B1 | 4/2002 | Christel et al. | |

(Continued)

FOREIGN PATENT DOCUMENTS

| | | |
|---|---|---|
| CN | 1871517 A | 11/2006 |
| CN | 101102847 A | 1/2008 |

(Continued)

OTHER PUBLICATIONS

Dickson, Mary Nora, et al., "Efficient capture of circulating tumor cells with a novel immunocytochemical microfluidic device", BioMicrofluidics 5, pp. 34119-15 (2011).

(Continued)

*Primary Examiner* — Gailene Gabel
(74) *Attorney, Agent, or Firm* — Cooley LLP

(57) ABSTRACT

The present invention provides a device for isolating target biomolecules or cells from samples, particularly biological samples. In particular, the device comprises a loading mixture, which contains the biological sample and a first binding entity that specifically binds to the target biomolecule or target cell; and a micro-channel coated with a second binding entity that binds directly or indirectly to the first binding entity. Methods of capturing, detecting, and/or evaluating target biomolecules or target cells (e.g. cancer cells) in biological samples are also disclosed.

12 Claims, 18 Drawing Sheets

Cells Pre-labeled with Ab Prior to Enrichment on Streptavidin Channel

Related U.S. Application Data

(60) Provisional application No. 61/298,871, filed on Jan. 27, 2010, provisional application No. 61/235,615, filed on Aug. 20, 2009, provisional application No. 61/163,009, filed on Mar. 24, 2009.

(51) Int. Cl.
  *G01N 33/569* (2006.01)
  *G01N 33/574* (2006.01)

(56) References Cited

U.S. PATENT DOCUMENTS

| | | | |
|---|---|---|---|
| 6,613,525 | B2 | 9/2003 | Nelson et al. |
| 6,893,881 | B1 | 5/2005 | Fodstad et al. |
| 7,195,872 | B2 * | 3/2007 | Agrawal ............ B01J 19/0046 422/503 |
| 8,008,032 | B2 * | 8/2011 | Forsyth ............... G01N 33/574 422/417 |
| 9,128,082 | B2 | 9/2015 | Mikolajczyk et al. |
| 9,671,407 | B2 | 6/2017 | Mikolajczyk et al. |
| 2002/0172987 | A1 | 11/2002 | Terstappen et al. |
| 2004/0197832 | A1 | 10/2004 | Amiel et al. |
| 2005/0123914 | A1 | 6/2005 | Katz et al. |
| 2005/0181429 | A1 | 8/2005 | Fejgin et al. |
| 2006/0000772 | A1 | 1/2006 | Sano et al. |
| 2006/0160243 | A1 | 7/2006 | Tang et al. |
| 2007/0161051 | A1 | 7/2007 | Tsinberg et al. |
| 2009/0215088 | A1 | 8/2009 | Allyn et al. |
| 2010/0255479 | A1 | 10/2010 | Mikolajczyk et al. |
| 2012/0100538 | A1 | 4/2012 | Mikolajczyk et al. |
| 2015/0056614 | A1 | 2/2015 | Mikolajczyk et al. |

FOREIGN PATENT DOCUMENTS

| | | |
|---|---|---|
| CN | 101374939 A | 2/2009 |
| GB | 2285863 A | 7/1995 |
| JP | H04-080657 A | 3/1992 |
| JP | 2000-508171 | 7/2000 |
| JP | 2003-075444 A | 3/2003 |
| JP | 2006-513695 | 4/2006 |
| JP | 2006-521821 | 9/2006 |
| JP | 2007-501407 | 1/2007 |
| JP | 2007-525642 | 9/2007 |
| JP | 2008-503498 | 2/2008 |
| WO | WO 1984/02193 | 6/1984 |
| WO | WO 00/00826 | 1/2000 |
| WO | WO 2003/020986 A1 | 3/2003 |
| WO | WO 2003/050537 | 6/2003 |
| WO | WO 2003/065042 | 8/2003 |
| WO | WO 2003/106495 | 12/2003 |
| WO | WO 2004/091384 A2 | 10/2004 |
| WO | WO 2004/076643 A2 | 11/2004 |
| WO | WO 2004/106925 | 12/2004 |
| WO | WO 2005/089253 | 9/2005 |
| WO | WO 2006/002114 | 1/2006 |
| WO | WO 2006/078470 A1 | 7/2006 |
| WO | WO 2006/119203 A2 | 11/2006 |
| WO | WO 2007/075270 | 7/2007 |
| WO | WO 2007/082302 | 7/2007 |
| WO | WO 2008/011486 | 1/2008 |
| WO | WO 2008/149803 | 12/2008 |
| WO | WO 2008/156906 | 12/2008 |
| WO | WO 2009/024691 | 2/2009 |
| WO | WO 2009/029601 | 3/2009 |
| WO | WO 2009/039507 A2 | 3/2009 |
| WO | WO 2010/111388 A2 | 9/2010 |

OTHER PUBLICATIONS

Gudrun Hager, Dan Cacsire-Castillo Tong, et al., The use of a panel of monoclonal antibodies to enrich circulating breast cancer cells facilitates their detection, <Gynecologic Oncology>, bol. 98, No. 2, Aug. 2005; p. 211-216.

Loo, et al., "Antibody-based identification of cell surface antigens: targets for cancer therapy", Current Opinion in Pharmacology, vol. 8, No. 5.

International Search Report and Written Opinion in PCT/US2010/028499 dated Dec. 23, 2010.

Supplementary European Search Report issued in EP 10756790.1 dated Aug. 13, 2012.

Office Action issued in CN Application No. 201080019566.9 dated Sep. 18, 2013 (and English translation).

Office Action issued in EP Application No. 10756790.1 dated Jun. 18, 2013.

Office Action issued in JP Application No. 2012-502208 dated Dec. 16, 2013 (and English translation).

Bischoff et al., Cell-free fetal DNA and intact fetal cells in maternal blood circulation: implications for first and second trimester non-invasive prenatal diagnosis, Human Reproduction Update, vol. 8, No. 6, 2002, pp. 493-500.

Hager, Gudrun et al., The use of a panel of monoclonal antibodies to enrich circulating breast cancer cells facilitates their detection, <Gynecologic Oncology>, bol. 98, No. 2, Aug. 2005; p. 211-216.

Holdenrieder et al., Apoptosis in Serum of Patients with Solid tumors, Anticancer Research, vol. 19, 1999, pp. 2721-2724.

Katz-Jaffe, DNA identification of fetal cells isolated from cervical mucus: potential for early non-invasive prenatal diagnosis, BJOG, vol. 112, May 2005, pp. 595-600.

Miller et al., Transcervical recovery of fetal cells from the lower uterine pole: reliability of recovery and histological/immunocytochemical analysis of recovered cell populations, Human Reproduction, vol. 14, No. 2, 1999, pp. 521-531.

Nagrath et al. Isolation of rare circulating tumour cells in cancer patients by microchip technology, Nature 450 (7173): 1235-1239 (Dec. 2007).

Int'l Preliminary Report on Patentability, PCT/US2007/066475, dated Oct. 14, 2008.

Int'l Preliminary Report on Patentability, PCT/US2008/077251, dated Mar. 24, 2010.

Int'l Search Report, W02009/039507 A3, dated Apr. 15, 2009.

Advisory Action in U.S. Appl. No. 12/730,738, dated Oct. 14, 2014.

European Search Report, EP appl. No. 15188374.1, 7 pages, dated Feb. 3, 2016.

Final Office Action in U.S. Appl. No. 12/730,738, dated May 5, 2014.

Office Action issued in U.S. Appl. No. 12/730,738 dated Aug. 7, 2013.

International Preliminary Report on Patentability in PCT/US2010/028499 dated Sep. 27, 2011, 4 pages.

* cited by examiner

DEVICES AND METHODS OF CELL CAPTURE AND ANALYSIS

RELATED APPLICATIONS

This application is a divisional of U.S. application Ser. No. 12/730,738, filed on Mar. 24, 2010, now U.S. Pat. No. 9,128,082, which claims priority to U.S. Provisional Application No. 61/235,615 filed Aug. 20, 2009; U.S. Provisional Application No. 61/163,009, filed Mar. 24, 2009, and U.S. Provisional Application No. 61/298,871, filed Jan. 27, 2010, each of which are hereby incorporated by reference in their entireties.

FIELD OF THE INVENTION

The present invention relates to micro-channel devices for capturing targets, such as cells and molecules of interest from solutions, as well as to post-capture analysis of circulating cells. In certain embodiments, the present invention relates to methods and devices for capturing target cells (e.g. circulating tumor cells) from physiological fluids, and analyses thereof.

BACKGROUND OF THE INVENTION

Isolation of target cells or molecules from heterogeneous samples remains a prominent interest for research applications as well as medical applications, such as diagnostics and therapeutics. In particular, separation of rare cell types from physiological tissues and bodily fluids obviates the need to obtain large tissue samples and avoids the risks associated with the procedures required to obtain such samples. For example, isolation of fetal cells from maternal blood samples for genetic testing avoids the risks associated with aminocentesis or chronic villus sampling. Isolation of circulating tumor cells from a patient would allow the clinician to evaluate the cancer and monitor pathological changes in the patient's tumor, as well as evaluate the efficacy of any on-going drug treatments without conducting invasive biopsy procedures.

Current methods for separating biological molecules and/or cells from heterogeneous samples typically entail the use of a high affinity binding partner (e.g. an antibody or antigen) coupled to a solid support. The heterogeneous sample is passed over the solid support and the target biological molecules or cells of interest are bound by the binding partner and retained on the solid support. The bound molecules or cells of interest can be subsequently analyzed for the presence of molecular genomic and proteomic information.

These current approaches suffer from several technical difficulties, one of which is the problem of non-specific binding. To minimize non-specific binding, one or more washing steps is required to remove other molecules and/or cells that are bound to the solid support or binding partner. In addition, the subsequent in situ analysis of cells on the channel by staining and hybridization procedures may subject the cells to harsh and denaturing conditions. These washing and analysis procedures can compromise the initial capture of the desired molecule or cell by subjecting the binding partner to conditions that may cause the binding partner to degrade, lose some of its conformational structure, or become detached from the solid support.

Further still, existing methods for analyzing circulating cells (e.g., as captured from a patient sample) for malignancy, such as staining cells for cytokeratin (CK), have limitations as markers for identifying and/or evaluating circulating tumor cells.

Thus, there is a need in the art for additional methods and devices for isolating biological molecules and/or cells of interest from samples, as well as methods for subsequent analysis of captured targets, such as analysis of captured, circulating tumor cells.

SUMMARY OF THE INVENTION

The present invention provides devices and methods for capturing and/or analyzing biological targets from fluid samples. In various embodiments, the invention provides methods for capturing circulating tumor cells from biological samples, for the evaluation of a cancer patient's disease. In these and other embodiments, the invention provides methods for identifying and/or evaluating circulating cells for malignancy without or independent of CK status.

In one aspect, the invention provides a method for capturing biological targets from solution. In this aspect, the present invention is based, in part, on the discovery that pre-labeling or pre-mixing a sample containing a target (e.g., a cell) of interest with a binding partner that specifically binds to the cell enhances the capture of such targets in a micro-channel device.

In certain embodiments, the device comprises a micro-channel and a loading mixture. The micro-channel may comprise a population of posts distributed on the surface of the micro-channel in random pattern. The loading mixture may comprise a biological sample suspected of containing a target, such as a target cell, and also comprises a first binding entity. The first binding entity specifically binds to the target (e.g., a target entity on a target cell). The surface of the micro-channel is coated with a second binding entity that specifically binds, directly or indirectly, to the first binding entity. In some embodiments, the loading mixture further comprises a third binding entity conjugated to a detectable or capturable entity. For example, the first binding entity may be a primary antibody, the third binding entity may be a secondary antibody that specifically binds to the primary antibody, and the second binding entity specifically binds directly or indirectly to the secondary antibody. In one embodiment, the third binding entity is a biotinylated secondary antibody that specifically binds to the first binding entity and the second binding entity is avidin. The secondary antibody may be intact antibody or any antibody fragment such as Fab'2, Fab' or Fab. In addition this may include any of the genetically engineered or expressed forms of antibody fragment such as single chain Fab fragment or single chain variable fragment.

In another aspect, the present invention provides a method for capturing and/or detecting a target cell in a biological sample, including rare cell populations as described herein. In one embodiment, the method comprises contacting a biological sample with a first binding entity to form a pre-loading mixture, wherein the first binding entity specifically binds to a target entity on the surface of the target cell; passing the pre-loading mixture through a micro-channel, wherein the surface of the micro-channel is coated with a second binding entity capable of specifically binding to the first binding entity; and detecting the presence of the target cell on the surface of the micro-channel. The biological sample can be a physiological or bodily fluid or tissue, such as blood, plasma, serum, bone marrow, semen, vaginal secretions, urine, amniotic fluid, cerebral spinal fluid, synovial fluid, fine needle aspirates (FNAs) or biopsy tissue sample. In certain embodiments, the target cell is rare and present at a low ratio in the biological sample. Examples of target cells that are rare in the biological samples (e.g., blood) include circulating tumor cells (CTCs), cells that are in early stages of a disease state such as Stage 1 of tumorigenesis, as well as viral-, bacterial-, or fungal-infected cells.

In certain embodiments, the target cell is a cancer cell (e.g., a circulating tumor cell), such as a breast cancer cell, a prostate cancer cell, a colorectal cancer cell, a lung cancer cell, a pancreatic cancer cell, an ovarian cancer cell, a bladder cancer cell, an endometrine or uterine cancer cell, a cervical cancer cell, a liver cancer cell, a renal cancer cell, a thyroid cancer cell, a bone cancer cell, a lymphoma cell, a melanoma cell and a non-melanoma skin cancer cell. The tumor may be an epithelial tumor. In such embodiments, the first binding entity can be an antibody that specifically binds to circulating epithelial cells. In one embodiment, the first binding entity is an epithelial cell adhesion molecule antibody (e.g., EpCAM). In these and other embodiments, the first binding entity is a biotinylated-antibody and the second binding entity is avidin. In various embodiments, the invention involves antibody cocktails as the first binding entity, so as to capture circulating tumor cells exhibiting a range of epithelial, mesenchymal, stem or progenitor cell characteristics.

In another embodiment of the invention, the pre-loading mixture further comprises a third binding entity. In such embodiments, the first binding entity may be a primary antibody, the third binding entity may be a secondary antibody conjugated to a detectable or capturable entity and the secondary antibody specifically binds to the first binding entity. A second binding entity specifically binds to the third binding entity via the capturable moiety. In certain embodiments, the third binding entity is a biotinylated secondary antibody that specifically binds to the first binding entity, and the second binding entity is avidin.

In some embodiments, the method further comprises, after cell capture, cross-linking the target cell bound to the surface of the micro-channel. Cross-linking reagents include protein cross-linking reagents, such as a hydrophilic homobifunctional NHS crosslinking reagent. In certain embodiments, the captured cells can be subjected to further analysis in the micro-channel or outside the channel post capture.

In another aspect, the invention provides a method for post-capture analysis of circulating cells, and in particular, to examine or evaluate the circulating cells for malignancy. Generally, the invention in this aspect involves evaluating captured cells for aneuploidy, optionally with evaluation of other markers of malignancy, including mutations. The method generally does not involve determining, or is independent of, cytokeratin expression.

DETAILED DESCRIPTION

Figure 1:
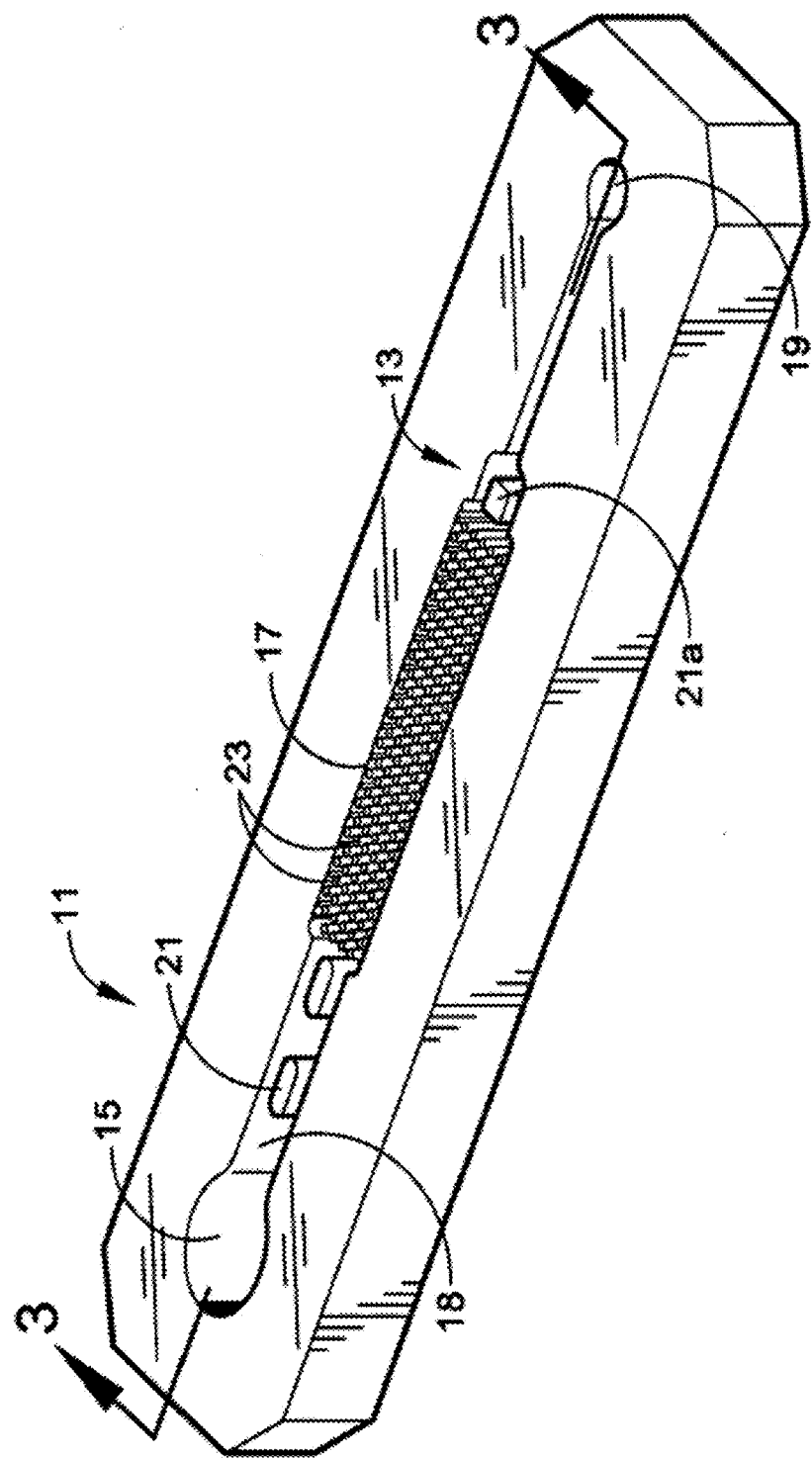
FIG. 1 is a perspective view of one embodiment of a micro-channel device comprising a post-containing collection region in the micro-channel.

The present invention provides devices and methods for capturing and/or analyzing biological targets from fluid samples. In various embodiments, the invention provides methods for capturing circulating tumor cells from biological samples, for the evaluation of a cancer patient's disease. In these and other embodiments, the invention provides methods for identifying and/or evaluating circulating cells for malignancy without or independent of cytokeratin expression.

In one aspect, the invention is based, in part, on the discovery that pre-labeling or pre-mixing a sample containing a target of interest with a binding partner that specifically binds to the target allows, e.g., enhances the capture of such targets in a micro-channel device, such as a microchannel device described herein. This approach also provides flexibility in the type and nature of primary antibodies that may be used to label cellular antigens. Accordingly, the present invention provides a novel device and method for separating biomolecules or cells of interest from samples, particularly biological samples. In one embodiment, the device comprises a micro-channel and a loading mixture. The micro-channel may comprise a population of posts distributed on the surface of the micro-channel in random pattern. The loading mixture may comprise a biological sample suspected of containing a target cell and a first binding entity, wherein the first binding entity specifically binds to a target entity on the target cell. The surface of the micro-channel is coated with a second binding entity that specifically binds to the first binding entity, either directly or indirectly.

Any suitable micro-channel device may be used in connection with the present invention. In some embodiments, the micro-channel device comprises a plurality of pre-determined flow paths. In some embodiments, the micro-channel device comprises posts or obstacles arranged in a random pattern or a regular or repeat pattern. In some embodiments, the micro-channel device comprises regions providing streamlined flow or random non-streamlined flow for any fluid passing through.

The micro-channel device may be a random-flow device for separating biomolecules or cells as described in detail in U.S. Published Application No. 2006/0160243, which is hereby incorporated by reference in its entirety. Such devices can be modified as described herein for use in connection with the invention. In general, the random-flow micro-channel device includes a substrate or support that has a flow path defined therein that includes at least one micro-channel having a collection region, which flow path is linked to a sample inlet and a liquid outlet. In some embodiments, the flow path may include several micro-channels, arranged in series, each of which has one such collection region. Alternatively, a random flow micro-channel may have more than one collection region, arranged in series, and there may also have more than one inlet and more than one outlet. One particular embodiment of the random flow micro-channel device is described in Example 1 and illustrated in FIG. 1.

The collection region of the random flow micro-channel can contain a plurality of upstanding posts that are aligned transverse to the liquid flow path and arranged in an irregular, random pattern across the entire width of the collection region portion of the flow channel. In one embodiment, the pattern of the posts is such that there can be no straight-line flow through the collection region and/or that streamlined flow streams are disrupted, assuring there is good contact between the liquid being caused to flow along the flow path and the surfaces of the posts. The posts in general are integral with the flat base of the collection region and extend perpendicular thereto, presenting surfaces that are vertical relative to a horizontal path of liquid being caused to flow through the flow channel of the substrate or support.

The placement and shape of the posts in the patterned post collection region can be engineered for optimal fluid dynamics and enhancement of capture of target cells through their specific surface characteristics. Very generally, in most instances, the preferred shape of the horizontal cross-section of the transverse fixed posts avoids sharp angles which might promote nonspecific binding to the transverse surfaces of the posts. The posts have rectilinear exterior surfaces and preferably have either a generally circular cross sectional shape or regular polygonal of 6 or more sides. Alternative shapes that might be used are a tear-drop shape where the tip is at the downstream end and shallowly curved, or oval shape; however, should more impact be desired, a square shape could be used. In one embodiment, the pattern of the posts should create a flow pattern in the liquid stream which enhances the capture of target cells by the second binding entity attached to the surfaces of the posts, the base and the facing surface. To achieve this end, the posts, e.g., should be of different sizes and be arranged in a set random pattern. A random pattern of posts of different cross sectional sizes, e.g. circular cross section posts of at least about 3 or 4 different sizes, about 70 to about 130 microns in diameter, in a collection region about 100 microns high where the minimum separation spacing between posts is 50 to 70 µm and preferably about 60 µm.

In some embodiments, the cross sectional area of the posts, which all have sidewalls formed by parallel lines which are perpendicular to the base, is such that they occupy between about 10 to 40% or about 15 to 25% of the volume of the collection region. Preferably the post pattern will be such that they occupy about 20% of the volume of the collection region, leaving a void volume for liquid flow of about 80%. The posts are substantially spaced apart from one another, e.g. by at least about 60 microns, and posts of different sizes are preferably located upstream and downstream of one another. Smaller posts may create eddy regions downstream of larger posts, and as a result of the flow pattern that is generated, the surfaces in the vicinity may show particular effectiveness in capturing target cells.

Generally, the substrate component of the micro-channel device can be made from any suitable laboratory-acceptable material, such as silicon, fused silica, glass and polymeric materials. It may be desirable to use a material that is optically transparent, particularly when a diagnosis function is desired to be optionally employed. In its simplest embodiment, the substrate carrying the fabricated micro-channel is sealed with a plate having a flat surface that will abut the facing surface of the substrate. Such plate may be fabricated from the same material or may simply be a cover plate made of glass. Suitable plastics which may be used include polydimethylsiloxane (PDMS), polymethylmethacrylate (PMMA), polycarbonate, polystyrene, polyethylene teraphthalate, as well as other polymeric resins well known for acceptable laboratory material usage. Such patterned substrates may be fabricated using any convenient method such as those selected from among conventional molding and casting techniques.

Substrates may be conveniently fabricated from polymeric materials using a master or negative mold structure, which can be created in a thick negative photoresist, using optical lithography, as well known in this art. For instance, the construction layer can be formed from a mixture of commercially available, standard grade epoxy resin (EPON SU-8) photoresist and hardener (SU-82025), which may be spun onto silicon wafer substrates at 2000 rpm to provide, for example, a 40 or 50 µm thick film of such photoresist. The thickness determines the height of the flow path in the collection region. The film is subjected to pre-exposure baking for 3 minutes at 60° C. and then 7 minutes at 95° C. on a precisely level hot plate to assure even thickness throughout, and the resultant samples are cooled to room temperature. A Karl Suss Contact Mask Aligner is used to expose a film with the desired pattern for the flow path in the ultimate device. The film is then post-baked at 65° C. for 2 minutes and then at 95° C. for 5 minutes before it is developed in a commercial SU-8 developer for 5 minutes, with light stirring being applied during developing. This creates a negative pattern mold in the epoxy resin photoresist that is then used as a molding master for replication of patterned post substrates in PDMS or other suitable polymeric resin. The layout and the dimensions of the microchannel and of patterned posts in the collection region are determined by the mask used in exposure step of the fabrication of the master mold. The depth of the microchannel is controlled by the thickness of the SU-8 layer of the master mold, which is determined by spin-coating conditions.

The invention further involves a loading mixture that comprises a biological sample suspected of containing a target (e.g., a target cell), and also comprises a first binding entity. The biological sample can include, but is not limited to, a physiological or bodily fluid or tissue or a cell mixture isolated from a biological sample. For example, the biological sample can include, without limitation, blood, plasma, serum, semen, vaginal secretions, urine, saliva, amniotic fluid, cerebral spinal fluid, synovial fluid, a fine needle aspirate (FNA), and a biopsy tissue sample. A target cell can be any cell comprising a detectable surface antigen, such as a cancer cell, stem cell, fetal cell, a viral-, a bacterial- or a fungal-infected cell. In some embodiments, the target cell is a cancer cell. In certain embodiments, the target cell is rare and is present at a low ratio in the biological sample, or expresses a very low level of a particular antigen of interest. Examples of target cells that are rare in the biological samples include circulating tumor cells (CTCs), cells that are in early stages of a disease state such as cells at Stage 1 of tumorigenesis, early viral-, bacterial-, or fungal-infections.

Preferably, the first binding entity specifically binds to a target entity on the target cell. The first binding entity can include, but is not limited to, an antibody, an antigen, an aptamer, a nucleic acid (e.g. DNA and RNA), a protein (e.g. receptor, enzyme, enzyme inhibitor, enzyme substrate, ligand), a peptide, a lectin, a fatty acid or lipid and a polysaccharide. In one embodiment, the first binding entity is an antibody. In another embodiment, the first binding entity comprises a binding entity mixture having at least a first antibody and a second antibody, and wherein the first antibody specifically binds to a first epitope of the target entity and the second antibody specifically binds to a second epitope of the target entity. The first binding entity can comprise a mixture of antibodies or binding entities directed to the one or more target antigens on the cell, or one or more epitopes of the target antigen, or a combination thereof. As used herein the term "epitope" can refer to a binding region on a singular antigen or a binding region on a second antigen. By way of example, in some embodiments, the first antibody binds to a first epitope on a first antigen and the second antibody binds to a second epitope on the first antigen. In other embodiments, the first antibody binds to a first epitope on a first antigen and the second antibody binds to a second epitope on a second antigen. In certain embodiments, the antibodies may be conjugated to a tag molecule including, but not limited to biotin, digoxigenin, FLAG epitope, or polyhistidine.

In another embodiment of the invention, the loading mixture further comprises a third binding entity conjugated to a detectable or capturable entity. For example, the first binding entity may be a primary antibody or ligand, the third binding entity is a secondary antibody or ligand that specifically binds to the first binding entity, and the second binding entity specifically binds to the third binding entity. A primary antibody can include a monoclonal antibody, a polyclonal antibody, or partially purified antibodies. The secondary antibody can be an antibody that binds to the constant region of the primary antibody. By way of example, if the primary antibody is a mouse antibody, the secondary antibody may be an anti-mouse antibody. The detectable or capturable entity conjugated to the secondary antibody can be a tag including, but not limited to, biotin, digoxigenin, FLAG epitope, or polyhistidine. In one embodiment, the loading mixture further comprises a third binding entity, wherein the first binding entity is a primary antibody, the third binding entity is a biotinylated secondary antibody that specifically binds to the first binding entity and the second binding entity is avidin. As used herein, the term "avidin" includes any expressed or engineered form of the avidin biotin-binding molecule, such as streptavidin, neutravidin and the like.

The surface of the micro-channel of the device is coated with a second binding entity that specifically binds to the first binding entity. The second binding entity can be an antibody, an antigen, an aptamer, a nucleic acid (e.g. DNA and RNA), a protein (e.g. receptor, enzyme, enzyme inhibitor, enzyme substrate, ligand), a peptide, a lectin, a fatty acid or a lipid, and/or a polysaccharide. The second binding entity may be the same type of molecule as the first binding entity (e.g. antibody-antibody or nucleic acid-nucleic acid) or it may be a different type of molecule than the first binding entity (e.g. nucleic acid-protein). The second binding entity can directly bind to the first binding entity or it can indirectly bind to the first binding entity through a tag molecule. For instance, if the first binding entity is a biotinylated primary antibody, the second binding entity can be avidin. In one embodiment, the second binding entity is avidin. In some embodiments, the loading mixture can comprise both a first binding entity and a third binding entity, wherein the first binding entity binds to a target entity (e.g., on the target cell) and the third binding entity specifically binds to the first binding entity. In such embodiments, the second binding entity specifically binds to the third binding entity either directly or indirectly through a detectable entity. By way of example, if the first binding entity is a mouse primary antibody and the third binding entity is an anti-mouse antibody conjugated to digoxigenin, then the second binding entity can be an anti-digoxigenin antibody.

The polymeric surface of the micro-channel and/or the patterned post or obstacle region comprised therein can be derivatized in various ways to enable the attachment of the second binding entity onto all the surfaces. For example, after plasma treatment and closure of the micro-channel-carrying substrate, a 1 to 50 volume % solution of an aminofunctional silane (e.g. a 3% solution of Dow Corning Z-6020), or a thio-functional silane, in ethanol may be injected into the micro-channel to fill the collection region between the sample inlet and sample outlet regions, and the flooded micro-channel can then be left to incubate for 30 minutes at room temperature. Derivitization can be performed on a non-fully cured polymer, such as PDMS, before the closure of the micro-channel region with a plate. In such case, an alternative is to slightly undercure the PDMS substrate and then complete the curing after affixing the seal plate and treating with the substituted silane or other functionalizing reagent. For example, a final heating step of about 90 minutes at about 50 to 90° C. might be used to complete the curing after treating with the Z-6020. Alternatively, one or two days at room temperature would also complete the curing. Such derivatization treatment can also be performed before the closure of the micro-channel region because derivatization of the facing flat surface is of no real consequence. The flow path is then purged with ethanol, and the micro-channel is ready for attachment of the second binding entity.

Second binding entities can be directly or indirectly immobilized upon the surfaces of the posts, obstacles, and/or the micro-channel, and the surfaces can be pre-treated and/or coated to facilitate attachment. In some embodiments, indirect immobilization is preferred and contemplates the employment of an intermediate agent or substance that is first linked to the post or surface. It may be desired to use coupling pairs to link to the intermediate agent. For example, avidin, or an antibody directed against another species antibody, might be attached to the intermediate agent, such as a NHS/maleimide heterobifunctional linker, which would thereafter couple to a biotinylated antibody or to an antibody of such other species.

Flow through the devices of the invention can be achieved by any suitable means, with or without exterior force. In one embodiment, flow through the devices of the invention is achieved by pumping, e.g. using a syringe pump or the like, or by vacuum that would draw liquid through from a reservoir at an inlet well provided by a large diameter inlet hole. Preferably such a well is included which has a capacity to hold about 50 µl to about 500 µl of liquid sample. In one embodiment, the design of the flow channel is such that, at flow rates through the device within a reasonable range (e.g. by injection of sample using a syringe pump or equivalent device, such as a Biocept syringe pump, or a standard Harvard Apparatus infusion syringe pump or other commercially available syringe pump) to create a flow in the collection region at a rate of about 0.01 to 100 mm per second, there is substantial disruption of streamlined flow through the region without creating turbulence. This results from the random arrangement of posts of different sizes and the relative spacing of the posts throughout the collection region. Relatively smooth, non-streamlined flow without dead spots is achieved at a preferred liquid flow rate of between about 0.3 to 10 mm/sec, and more preferably the flow rate is maintained between about 0.5 and 5 mm/sec and is achieved by suction from an inlet well of defined size.

The present invention also provides a method for detecting a target cell in a biological sample using the devices described herein. For example, the method may comprise contacting a biological sample with a first binding entity to form a pre-loading mixture, wherein the first binding entity specifically binds to a target entity on the surface of the target cell, passing the pre-loading mixture through a micro-channel, wherein the surface of the micro-channel is coated with a second binding entity capable of specifically binding to the first binding entity, and detecting the presence of the target cell on the surface of the micro-channel. In certain embodiments, the micro-channel comprises a population of posts distributed on the surface of the micro-channel in random pattern.

Various types of biological samples, such as blood, plasma, serum, bone marrow, semen, vaginal secretions, urine, saliva, amniotic fluid, cerebral spinal fluid, synovial fluid, lung lavages, fine needle aspirates (FNAs) and biopsy tissue samples, are suitable for use in the methods of the invention. In one embodiment, the biological sample is a blood sample from a patient. The target cell can be present in the biological sample in the ratio of 1 out of $10^{10}$ cells, 1 out of $5 \times 10^7$, or 1 out of $10^4$ cells. A target cell can be any cell comprising a detectable surface antigen, such as a cancer cell, stem cell, fetal cell, a viral-, a bacterial-, or a fungal-infected cell.

In one particular embodiment, the target cell is a cancer cell. The cancer cell can be a cell from any type of cancer, such as an epithelial cancer, including, but not limited to, breast cancer cells, prostate cancer cells, colorectal cancer cells, lung cancer cells, pancreatic cancer cells, ovarian cancer cells, bladder cancer cells endometrial or uterine cancer cells, cervical cancer cells, liver cancer cells, renal or kidney cancer cells, thyroid cancer, bone cancer cells, lymphoma cells (e.g. Hodgkin's lymphoma, non-Hodgkin's lymphoma), melanoma cells, and non-melanoma skin cancer cells.

The first binding entity can be any of the molecules as described herein. In one embodiment, the first binding entity is an antibody. The first binding entity may be a biotinylated-antibody and the second binding entity may be avidin. In some embodiments, the first binding entity can be an antibody that specifically binds to circulating epithelial cells. The antibody can be an epithelial cell adhesion molecule (EpCAM) antibody, such as an antibody that specifically binds to an epithelial cell surface adhesion protein. The first binding entity may be a cocktail of two, three, four, five, or more antibodies, for example, as described herein for capture of target cancer cells. For example, the antibody cocktail may comprise at least antibody against an epithelial cell surface antigen, and at least one antibody against an antigen that is indicative of a mesenchymal phenotype, to thereby isolate cells having a range of epithelial and/or mesenchymal characteristics from the sample.

For example, where the target cell is a breast cancer cell, the first binding entity may be an antibody that specifically binds to EpCAM (epithelial cell adhesion molecule), Her2/neu (Human Epidermal growth factor Receptor 2), MUC-1, EGFR (epidermal growth factor receptor), TAG-12 (tumor associated glycoprotein 12), IGF1R (insulin-like growth factor 1 receptor), TACSTD2 (tumor associated calcium signal transducer 2), CD318, CD340, CD104, N-cadherin or a combination (e.g., cocktail) of two or more thereof.

In yet another embodiment, the target cell is a prostate cancer cell and the first binding entity is an antibody that specifically binds to EpCAM, MUC-1, EGFR, PSMA (prostate specific membrane antigen), PSA (prostate specific antigen), TACSTD2, PSCA (prostate stem cell antigen), PCSA (prostate cell surface antigen), CD318, CD104, N-cadherin or a combination thereof. In another embodiment, the target cell is a colorectal cancer cell and the first binding entity is an antibody that specifically binds to EpCAM, CD66c, CD66e, CEA (carcinoembryonic antigen), TACSTD2, CK20 (cytokeratin 20), CD104, MUC-1, CD318, N-cadherin or a combination thereof.

In still another embodiment, the target cell is a lung cancer cell and the first binding entity is an antibody that specifically binds to CK18, CK19, CEA, EGFR, TACSTD2, CD318, CD104, or EpCAM or a combination thereof. In another embodiment, the target cell is a pancreatic cancer cell and the first binding entity is an antibody that specifically binds to MUC-1, TACSTD2, CEA, CD104, CD318, N-cadherin, EpCAM or a combination thereof. In yet another embodiment, the target cell is an ovarian cancer cell and the first binding entity is an antibody that specifically binds to MUC-1, TACSTD2, CD318, CD104, N-cadherin, EpCAM or a combination thereof.

In another embodiment, the target cell is an endothelial bladder cancer cell and the first binding entity is an antibody that specifically binds to CD34, CD146, CD62, CD105, CD106, VEGF receptor (vascular endothelial growth factor receptor), MUC-1 or a combination thereof. In another embodiment, the target cell is an epithelial bladder cancer cell and the first binding entity is an antibody that specifically binds to TACSTD2, EpCAM, CD318, EGFR, 6B5 or Folate binding receptor.

The target cell may be a cancer stem cell, and the first binding entity may be an antibody that specifically binds to CD133, CD135, CD117, CD34 or a combination thereof.

In some embodiments, the target cell is a circulating cancer cell that expresses mesenchymal antigens and the first binding entity is an antibody (or antibody cocktail) that specifically binds to FGFR1, FGFR4, EGFR, N-cadherin, folate binding receptor, and MSC or a combination thereof.

In some embodiments, the target cell is a circulating cancer cell that expresses angiogenesis surface antigens and the first binding entity includes an antibody that specifically binds to a VEGF receptor.

In other embodiments, the target cell is a melanoma cancer cell and the first binding entity is an antibody that specifically binds to one or more of the melanocyte differentiation antigens, oncofetal antigens, tumor specific antigens, SEREX antigens or a combination thereof. Examples of melanocyte differentiation antigens, include but are not limited to tyrosinase, gp75, gp100, Melan A/MART 1 or TRP-2. Examples of oncofetal antigens include antigens in the MAGE family (MAGE-A1, MAGE-A4), BAGE family, GAGE family or NY-ESOT. Examples of tumor-specific antigens include CDK4 and β-catenin. Examples of SEREX antigens include D-1 and SSX-2.

In certain embodiments, the first binding entity is an antibody directed to mutated peptides that are activated as a result of cellular transformation. These peptides include but are not limited to mutated introns, N-acetylglucosaminyltranferase, V gene product, MUM-1 and p15.

In other embodiments, the first binding entity is an antibody that recognizes the ganglioside, GM2, GD2, GM3 and/or GD3; high molecular weight chondroitin sulfate proteoglycan, CD146, or p97 melanotransferrin.

In certain embodiments, the target cell is a circulating tumor cell (CTC). A CTC in the blood sample is a tumor cell is often defined by staining positive for CK and DAPI and is staining negative for CD45 ($CK^+$, $CD45^-$, $DAPI^+$), whereas lymphocytes are $CD45^+$. Detection of the CTCs in the blood circulation can aid disease management, including the ability to monitor treatment efficacy or failure. However, due to the limited number of available CTC-specific antibodies, CTCs have failed to be captured in about 40%-60% of patient blood samples. Accordingly, the present invention in some aspects provides a method for capturing and detecting these rare CTCs.

In some embodiments, the first binding entity is a mixture (e.g., cocktail) of at least a first antibody and a second antibody, wherein the first antibody specifically binds to a first epitope of the target entity and the second antibody specifically binds to a second epitope of the target entity. The first and second epitopes can be present on the same antigen (molecule) or the first and second epitopes can be present on different antigens (molecules).

In one embodiment, the first binding entity can be a mixture of a first antibody and a second antibody, wherein the first antibody specifically binds to a stem cell antigen and the second antibody specifically binds to a cancer cell antigen. Stem cell antigens can be present on cancer stem cells, and antibodies directed to these stem cell antigens can be added as general capture antibodies to one or more antibodies directed to cancer antigens, such as those described herein. In some embodiments, the first antibody specifically binds to CD133, CD135, CD117, CD34 or combinations thereof, and the second antibody specifically binds to a cancer antigen.

In another embodiment, the first binding entity can be a mixture of a first antibody and a second antibody, wherein the first antibody specifically binds to a mesenchymal marker and the second antibody specifically binds to a cancer cell antigen. Circulating tumor cells can downregulate epithelial markers and upregulate mesenchymal markers, and thus can be captured by antibodies that specifically bind to such mesenchymal markers. In some embodiments, the first antibody specifically binds to FGFR1 (fibroblast growth factor receptor 1), FGFR4, MSC (mesenchymal stem cell antigen), EGFR, N-cadherin, folate binding receptor or combinations thereof, and the second antibody specifically binds to a cancer antigen.

In still another embodiment, the first binding entity can be a mixture of a first antibody and a second antibody, wherein the first antibody specifically binds to an angiogenesis marker and the second antibody specifically binds to a cancer cell antigen. In certain embodiments, the first antibody specifically binds to a VEGF receptor, and the second antibody specifically binds to a cancer antigen.

In another embodiment of the invention, the method further comprises contacting the pre-loading mixture with a third binding entity. The first binding entity may be a primary antibody, the third binding entity may be a secondary antibody conjugated to a detectable or capturable entity, and the secondary antibody specifically binds to the first binding entity. The second binding entity specifically binds to the third binding entity (e.g., via the capturable entity). In another embodiment, the method further comprises contacting the pre-loading mixture with a third binding entity, wherein the first binding entity is a primary antibody, the third binding entity is a biotinylated secondary antibody that specifically binds to the first binding entity, and wherein the second binding entity is an avidin molecule. The secondary antibody may be a whole or an intact antibody, or fragment thereof, such as Fab'2, Fab' or Fab, or any antibody derivatives. A derivatized antibody can be a fragment of the antibody, an antibody that has been conjugated to a fatty acid, carbohydrate, peptide, a chemical entity such as a fluorescein, streptavidin etc. A derivatized antibody can be an antibody where the amino acids have been modified to increase the avidity or affinity of the antibody to the target protein.

In some embodiments, the method further comprises cross-linking the target cell bound to the surface of the micro-channel. Several cross-linking agents can be employed to cross-link the bound target cells to the micro-channel, for example via, amino groups (amide, amine etc.), carbonyl groups, acyl groups, akyl groups, aryl groups, sulfhydryl groups, and others that are well known to one skilled in the art. Examples of cross-linking agents include, but are not limited to, hydrophilic homobifunctional NHS crosslinking reagents (e.g. Bis(NHS)PEO-5 (bis N-succinimidyl-[pentaethylene glycol] ester) to crosslink primary amines, homobifuctional isothiocyanate derivatives of PEG or dextran polymers, glutaraldehyde, heterobifunctional crosslinkers containing NHS on one end and maleimide on the other end of the polymer; peroxide treated carbohydrate polymers to form reactive aldehyde polymers, and EDC (1-Ethyl-3-[3-dimethylaminopropyl]carbodiimide hydrochloride) to crosslink carboxyl groups to primary amines. The length of the cross-linkers may be varied by adding one or more polymeric units between the two reactive groups on either end of the linker. Suitable polymeric units include, but are not limited to polymeric ethylene glycol, carbon chains, polynucleotides, polypeptides, and polysaccharides.

The cross-linking reagent can be applied to the micro-channel following capture of the target cells. In some embodiments, a second cross-linking treatment is employed following labeling (e.g. fluorescent labeling) of the captured cells to cross-link the label to the captured cells. The concentration of the cross-linking agent and duration of treatment will depend on the type and reactivity of cross-linking reagent, type of target cell, binding entities employed to capture the cells, and expression level of surface antigen to which a binding entity binds. Suitable concentrations can be from about 0.01 mM to about 10 mM, more preferably from about 0.5 mM to about 5 mM, or most preferably about 1 mM. Duration of treatment with the cross-linking reagent can be from about 5 min to about 120 min, about 15 min to about 90 min, or about 30 min to about 60 min. Optimization of the concentration of cross-linking reagent and duration of treatment is within the skill of the ordinary artisan.

Detecting the presence of captured cells can be by one of several methods known to those skilled in the art. In one embodiment, captured cells can be visualized by photomicroscopy. In another embodiment, captured cells may be labeled with a fluorescent molecule or stained and visualized by fluorescent microscopy or by measuring a fluorescent signal. For instance, captured cells may be stained with the nuclear dye DAPI and subsequently visualized by fluorescence microscopy. In another embodiment, detecting the presence of the target cell is carried out by detecting the presence of the first binding entity. Detection of the first binding entity can include exposing the captured cells to a tagged molecule that recognizes and binds the first binding entity. For example, the tagged molecule may be an antibody labeled with a fluorescent tag or colored latex particle that binds to the first binding entity. In one embodiment, the first binding entity is a biotinylated antibody and the tagged molecule is fluorescently labeled avidin. In some embodiments, the tagged molecule may be the same type of molecule as the second binding entity. In embodiments where a third binding entity is present, the detection of the captured cells can comprise detecting the presence of the third binding entity. In such embodiments, the tagged molecule recognizes and binds to the third binding entity. For example, the first binding entity can be a mouse antibody, the third binding entity can be a biotinylated secondary antibody that binds to mouse antibodies (e.g. a goat derived anti-mouse antibody), and the tagged molecule can be either a fluorescently labeled avidin or a fluorescently labeled antibody that binds to the third binding entity (e.g. a rabbit derived anti-goat antibody).

In some embodiments, subsequent analysis of the captured cells may be desired. In one embodiment, captured cells can be released from the micro-channel and collected for further analysis. Several methods for releasing the captured cells are known in the art and can include mechanical means (e.g. high fluid flow), chemical means (e.g. change in pH), or use of enzymatic cleavage agents. For example, a reagent may be applied to the micro-channel to cleave the second binding entity or to cleave the bond between the second binding entity and the cells in order to release the target cells from the micro-channel. For instance, trypsin, proteinase K, collegenase, or a specifically focused enzyme may be used to degrade the second binding entity (e.g. antibodies, streptavidin) and/or the cell surface antigens. During such cleavage, the outlet from the micro-channel is connected to a reservoir or other collector, and the discharge stream carrying the released cells is collected for further analysis. Such further analysis may include, but is not limited to, detection of aneuploidy (including monosomy or trisomy of, for example, chromosomes 1, 3, 4, 7, 8, 11, and/or 17), gene amplification, detection of gene mutation, gene duplication and other nucleic acid or protein changes well known in the art. For example, a gene mutation can be a substitution, addition, deletion of one or more nucleotides in a gene sequence. In one embodiment, the nucleic acid, such as DNA or RNA, obtained from the released cells can be subjected to fluorescent in-situ hybridization (FISH), PCR analysis, RFLP (restriction fragment length polymorphism) analysis, DNA sequencing, etc. In another embodiment, proteins or glycoproteins, including peptides and amino acids obtained from the released cells can be subjected to, for example but not limited to, amino acid or peptide analysis or sequencing, GC-MS and other techniques known to those skilled in the art of protein analyses. In yet another embodiment, the captured cell released from the micro-channel device can be analyzed morphologically by light microscopy, electron microscopy, scanning microscopy, immunocytochemistry staining (ICC) for internal cellular structures or surface proteins expression, etc.

In another embodiment, the captured cells may be further analyzed in situ. For example, the cells may be counted while attached, labeled with fluorescent markers, subject to in situ hybridization analysis, such as FISH. Because antibody-antigen bonds are not covalent, they can be dissociated under some circumstances. Therefore, in some embodiments, it is highly desirable to further stabilize the cells on the micro-channel by crosslinking the cells to the channel so that cells are not dislodged and lost during the various in situ labeling, heating, denaturing and washing steps. Cross-linking can be a particularly important consideration with cells that express a low level of the surface antigens targeted by the first binding entity since these cells can be more weakly attached to the second binding entity. Covalent crosslinking of the cells to the channel surface matrix can stabilize captured cells during post-capture analysis.

In another aspect, the invention provides a method of post-capture analysis of circulating cells. The circulating cells may be captured as described herein, including by the methods or devices of the invention. In some embodiments, the circulating cells are captured and evaluated without one or more enrichment and/or cell replicating or duplicating processes, e.g., via cell culture, etc. In this aspect, circulating cells are evaluated for malignancy independent of CK status or expression, e.g., without CK staining and/or any other evaluating assay. For example, in accordance with this aspect, captured cells are evaluated (as described herein) for aneuploidy. The aneuploidy may be with respect to, for example, chromosomes 1, 3, 4, 7, 8, 11, and/or 17. In certain embodiments, the invention involves evaluating circulating cells for monosomy or trisomy 8, 11, and/or 17. In certain embodiments, the invention involves evaluating circulating cells for monosomy 8, 11, and/or 17. Aneuploidy may be detected using any know method, such as FISH. Additionally markers of cancer or malignancy may be used (except cytokeratin expression), such as those described herein, including Her2 expression.

This invention is further illustrated by the following additional examples that should not be construed as limiting. The contents of all references, patents and published patent applications cited throughout this application, as well as the Figures, are incorporated herein by reference in their entirety.

EXAMPLES

Example 1. Construction of Basic Micro-Channel Device

One embodiment of a micro-channel device for separating biomolecules or cells is shown in FIG. 1. The device comprises a substrate or support 11 which is formed with a flow path that includes a micro-channel 13 to which sample liquid is to be supplied through an opening or well 15 that serves as an entrance or inlet at a first end of the device and an opening 19 that serves as an outlet at the second end of the device. The cross-section of the collection region 17 is greater than that of an inlet section 18 that leads there into from the inlet opening 15. The inlet section contains one or more pairs of axially aligned divider/supports 21 just upstream of where it widens at the end of the region 18 to enter the collection region 17. These central dividers break the flow into two or more paths and serve to distribute the flow of liquid more evenly as it is delivered to the entrance end of the collection region 17. The collection region contains a plurality of upstanding posts 23 that are aligned transverse to the liquid flow path and arranged in an irregular, generally random pattern across the entire width of the collection region portion of the flow channel. The pattern of the posts is such that there can be no straight-line flow through the collection region and that streamlined flow streams are disrupted, assuring there is good contact between the liquid being caused to flow along the flow path and the surfaces of the posts. The posts are integral with the flat base of the collection region 17 and extend perpendicular from the base, presenting surfaces that are vertical relative to a horizontal path of the liquid being caused to flow through the flow channel of the substrate 11. Another flow divider/support 21a is located at the exit from the collection region.

The substrate is formed from PDMS and is bonded to a flat glass plate to close the flow channel. The interior surfaces throughout the collection region are derivatized with amine groups (Inventors: Is the amine group specific to PDMS or can there be other active groups, e.g. SH— that can be derivatized. I seem to remember one can coat supports with polylysine to attach cells or positively charged proteins) by incubating for 30 minutes at room temperature with a 3% solution of 3-aminopropyltriethoxysilane. After washing with ethanol the amine groups on the channel are derivatized for 30 minutes with bifunctional PEG linker molecule containing an NHS ester on one end and a maleimide group on the other end. In this reaction the NHS group reacts with the amine groups on the channel. After washing the channel with PBS a solution of 0.5 mg/mL thiolated streptavidin is added which will react with the maleimide groups on the other end of PEG linkers attached to the channel. Thiolated streptavidin is prepared by treatment of streptavidin with Traut's reagent as is commonly known in the art. After incubation for 60 min, the excess thiolated streptavidin is washed from the micro-channel with PBS/1% BSA and stored for future use.

In a typical example, 10 mLs of blood is obtained and the buffy coat is isolated by density gradient sedimentation as is commonly known in the art. The buffy coat contains the nucleated white blood cell fraction of the blood and also contains epithelial or other nucleated cells present in the blood. The buffy coat contained in a volume of approximately 0.5 mL in a centrifuge tube is incubated with the first binding entity of the present invention for 30 min, and then the tube is filled with approximately 30-fold excess of PBS/BSA and centrifuged to pellet the buffy coat cells. The sample is resuspended in approximately 200 µL and passed through the avidin-coated micro-channel by hooking the micro-channel device up to outlet tubing from a syringe pump which is filled with about 50 µL of the cell suspension. The syringe pump is operated to produce a slow continuous flow of the sample liquid through the micro-channel device at room temperature and a rate of about 10 µL/min. During this period, the avidin attached to the surfaces in the collection region where the random pattern of transverse posts are located, captures the target cells of interest in the sample. After the entire sample has been delivered by the syringe pump, a slow flushing is carried out with a PBS/1% BSA aqueous buffer. About 100 µL of this aqueous buffer is fed through the device over a period of about 10 minutes, which effectively removes all non-specifically bound biomaterial from the flow channel in the device. Two additional washings are then carried out, each with about 100 µL of PBS/1% BSA over a period of about 10 minutes.

At this time, inasmuch as the device is made of optically clear material, microscopic examination can be made of the effects of the capture using photomicroscopy. Captured cells may be treated further with additional antibodies and fluorescent probes and analyzed by fluorescence microscopy.

Figure 2:
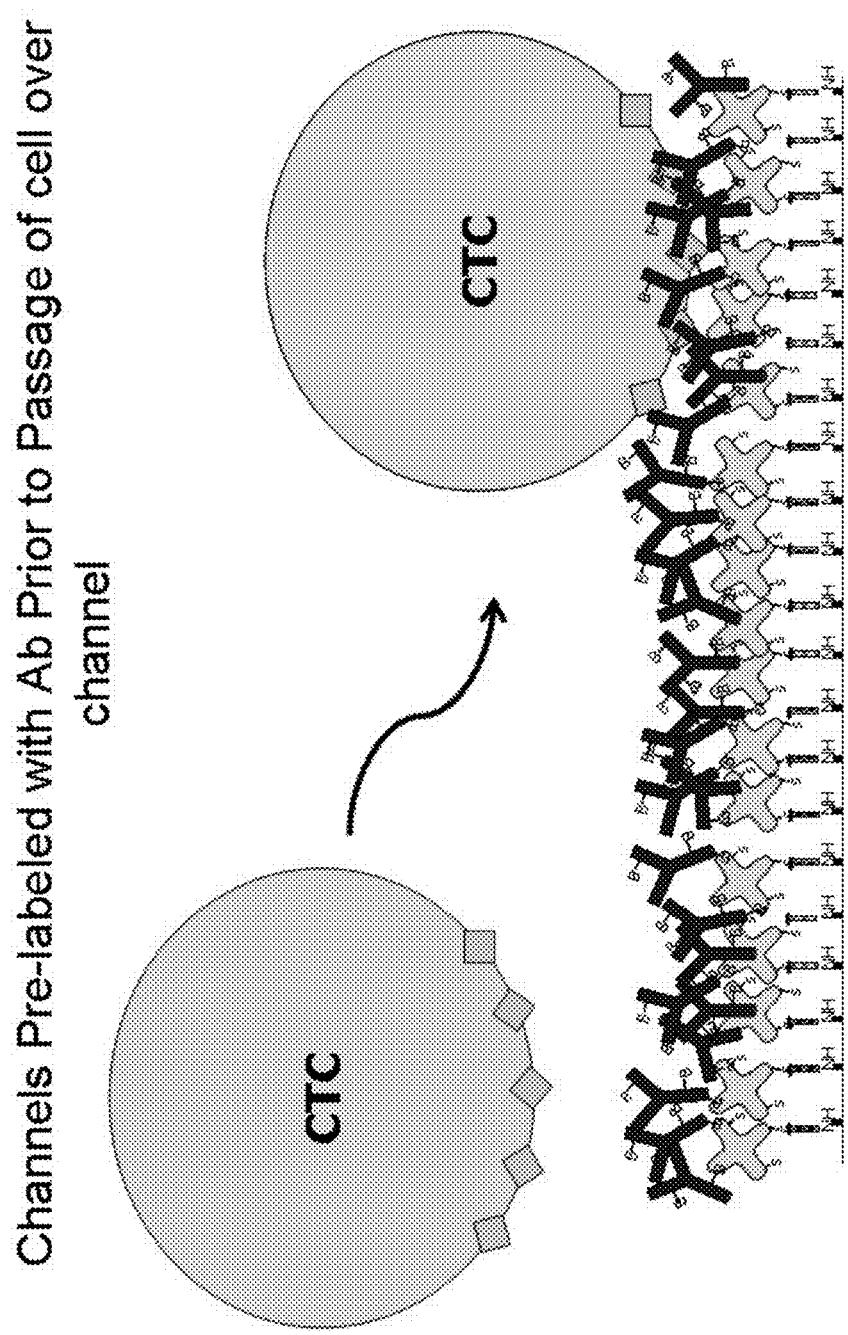
FIG. 2 is a schematic depicting capture of a circulating tumor cell (CTC) in a micro-channel device that has been coated with an antibody specific to an antigen on the CTC. B designates biotin.

Example 2. Comparison of Cell Capture Rates Between Pre-Labeled Micro-Channels and Pre-Labeled Cells As described in U.S. Published Application No. 2006/0160243, filed Jan. 18, 2005 and elsewhere (Nagrath et al. (2007) Nature, Vol. 450(7173):1235-9), previous devices for capturing cells of interest comprised a micro-channel that was derivatized with an antibody that was specific to antigens on the cells of interest. The suspension containing the rare cells of interest was then passed through the channel and cells were captured by the cell-specific antibody (FIG. 2).

While the level of antigen expression can be determined in cultured cells and on clinical tissue samples such as tumors, it is not known precisely how many antigens are available on the surface of a circulating tumor cell (CTC). It is known that tumors are highly heterogeneous and that cells detached from the tumor into the blood can change their expression levels of antigen. Therefore, it is most likely that CTCs are a highly heterogeneous population with specific antigen levels varying from very low to very high in any given sample. To obtain maximum capture of CTCs from a sample, it is best to optimize the system to capture cells with the lowest antigen expression levels.

Figure 3:
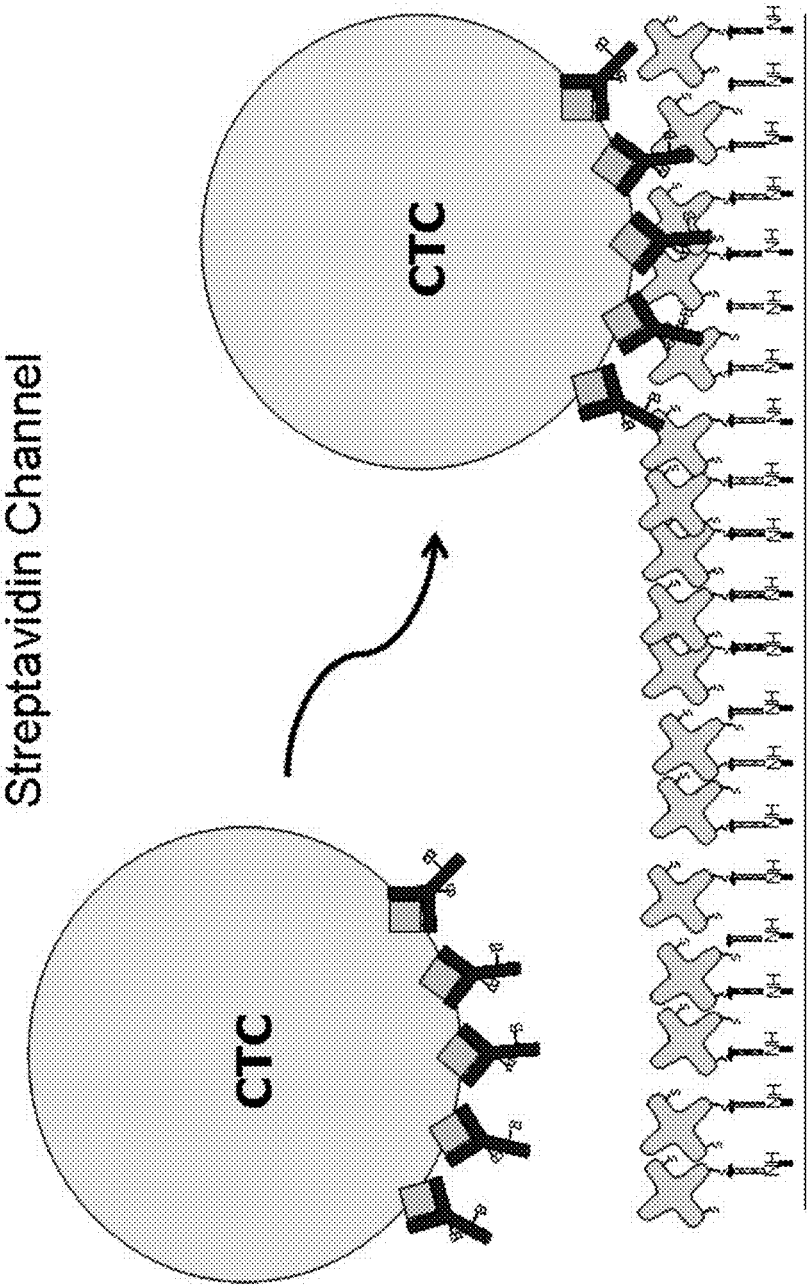
FIG. 3 is a schematic depicting capture of a circulating tumor cell (CTC) in a micro-channel device where the CTC has been pre-labeled with an antibody specific to a CTC antigen and the micro-channel device has been coated with a protein capable of binding the cell-specific antibody. B designated biotin.

The devices of the present invention comprise a micro-channel derivatized with a general antibody or protein that can bind to cell-specific antibodies as described in Example 1. The cell-specific antibody is added to the sample containing the cells of interest prior to passing the sample through the micro-channel, thus pre-labeling the cells. The cells of interest are then captured when the general antibody or other protein coating the channel binds to the cell-specific antibody bound to the cells of interest (FIG. 3).

The following set of experiments were conducted to determine whether pre-labeling a sample containing CTCs with antigen-specific antibodies result in a better capture rate on micro-channel devices as compared to micro-channel devices coated with the antigen-specific antibody. A common antigen used to capture CTCs is EpCAM, an epithelial cell surface adhesion molecule. For these experiments, the bladder cell line, T24, was used, which is known to express low levels of EpCAM.

In the traditional device, the micro-channel was derivatized with streptavidin and then biotinylated antibody for EpCAM was pre-loaded onto the channel (EpCAM channel). The EpCAM antibody was able to bind the EpCAM antigen on the surface of the T24 cells, thus capturing the cells in the micro-channel. In the device of the present invention, the micro-channel was derivatized with streptavidin (Strep channel) and the biotinylated antibody for EpCAM was incubated with the sample of T24 cells at approximately 1 μg/mL for 30-60 mins. prior to passage of the cells over the streptavidin-coated channel. The streptavidin binds to the biotinylated EpCAM antibody bound to the surface of T24 cells, thus capturing the cells in the micro-channel. Thus the reagent components of the two devices are identical except that they are applied to the devices in a different order.

Figure 4:
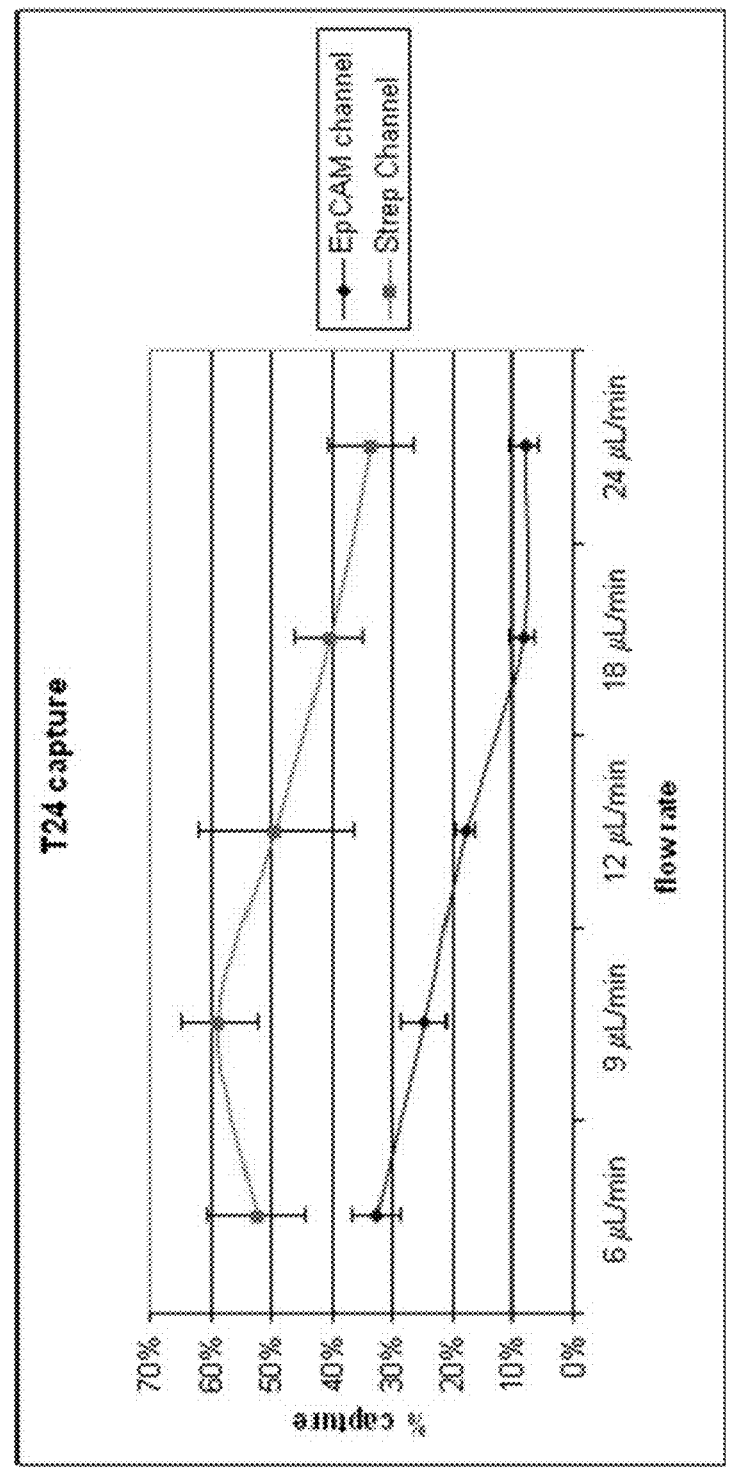
FIG. 4 is a graph showing percentage of T24 EpCAM positive cells captured on either a micro-channel coated with EpCAM antibodies (EpCAM channel) or a micro-channel coated with streptavidin (Strep channel) at different flow rates. In the case of the Strep channel, the T24 cells were pre-labeled with a biotinylated EpCAM antibody prior to passage over the Strep channel.

As shown in FIG. 4, use of the streptavidin-coated channel with cells pre-incubated with the biotinylated EpCAM antibody unexpectedly produced capture percentages about twice as high as those obtained with the EpCAM channel and unlabeled cells. The increased capture percentage is about 2-3 fold higher when cells are passed through the channel under multiple flow rates.

Figure 5:
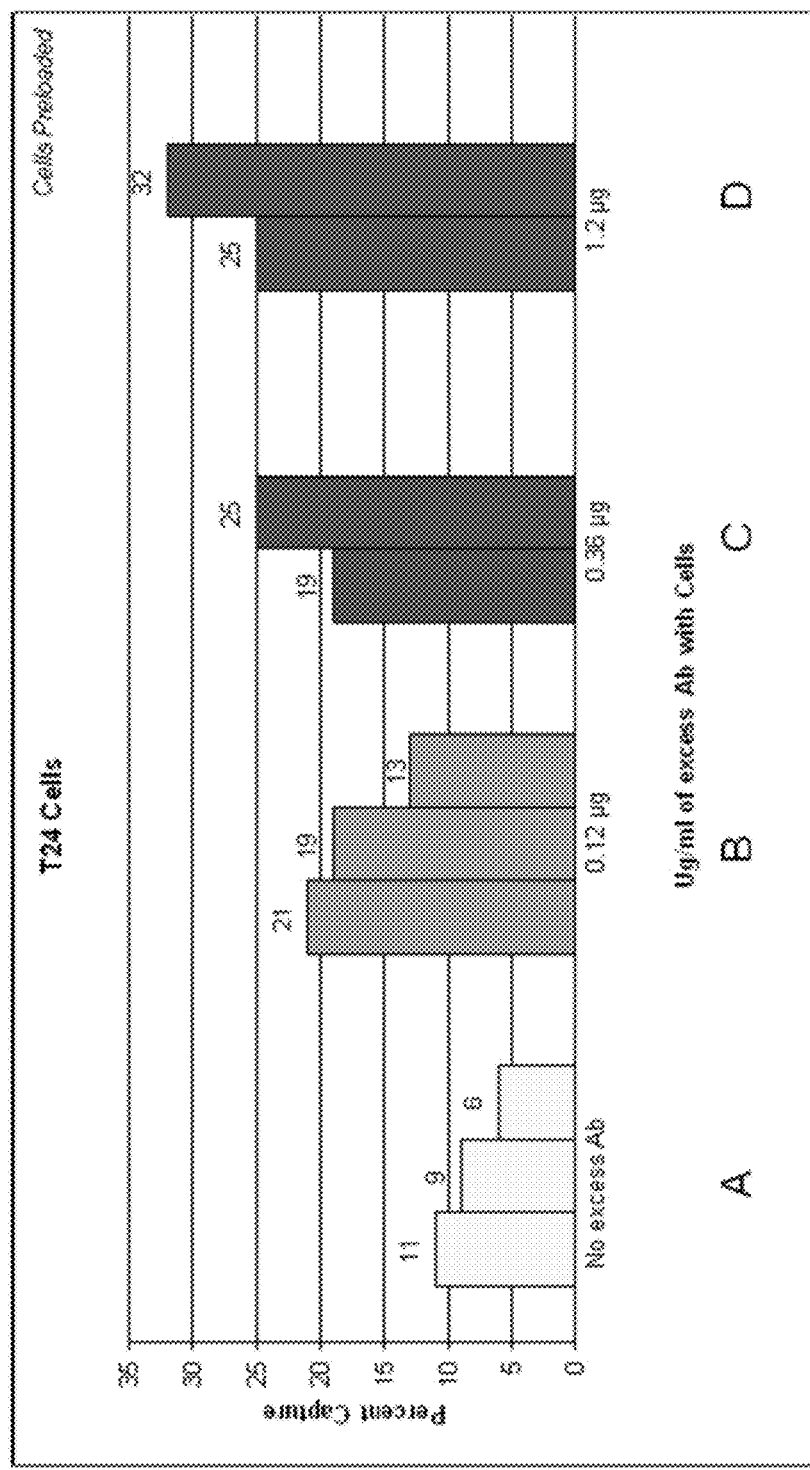
FIG. 5 is a graph showing the percentage of T24 cells pre-labeled with biotinylated EpCAM that were captured on a micro-channel coated with stretpavidin in the presence of different concentrations of excess biotinylated EpCAM antibody. A sample of 250 µL containing approximately 200 cells was applied to the channel.

In a next series of experiments, 1.2 μg/mL of the biotinylated-EpCAM antibody was pre-incubated with the cells for 30 mins. This concentration of antibody was about 100 to 1000 fold molar in excess over the total antigens present on the T24 cells and therefore, significant excess antibody remained in each suspension. After a 30 mins. incubation, the excess antibody was diluted to less than 0.05 μg/mL by dilution of the cells to approximately 200 cells for application on the channel. This sample of cells served as a control sample and was applied directly to the channel in 250 μL PBS/BSA (sample A in FIG. 5). In samples B-D excess antibody at the indicated concentrations were added back to the 250 μL cell suspension prior to running on the channel. As shown in FIG. 5, free antibody does not interfere with binding to the streptavidin on the channel, and does not decrease cell capture as expected, but in fact increases cell capture.

Figure 6:
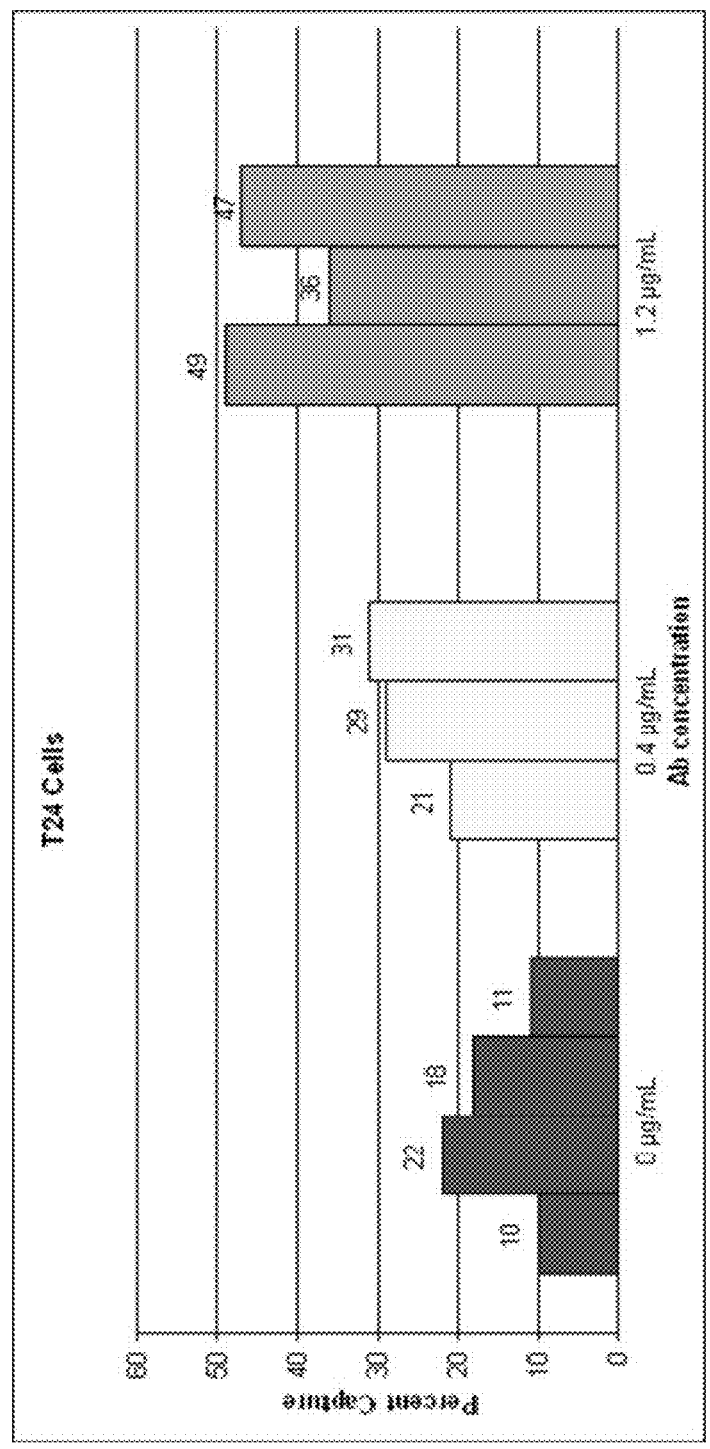
FIG. 6 is a graph showing the percentage of T24 cells pre-labeled with biotinylated EpCAM that were captured on a micro-channel coated with stretpavidin in the presence of different concentrations of excess biotinylated EpCAM antibody. A sample of 2 mL containing approximately 200 cells was applied to the channel.

In a similar experiment, the volume of the initial cell suspension applied to the channel was increased from 250 μl to 2 mL. Since the μg per mL of the added extra antibody remained the same as in FIG. 5, the total μg of absolute antibody in the sample with approximately 200 cells was nearly 10 times higher than in FIG. 5. As shown in FIG. 6, the added extra antibody shows a similar increase in cell recovery relative to the concentration of the antibody that was observed in the results depicted in FIG. 5. This result indicates that the observation of higher recovery is related to the concentration of excess antibody in the cell suspension and not the absolute μg of total antibody in the cell suspension.

The results of this series of experiments show unexpected advantages in collecting cells of interest in a micro-channel flow device when the cells are pre-labeled with antibody. As seen in FIG. 4, pre-incubating the cells with antigen-specific antibody significantly improves capture in the micro-channel device as compared to capture in micro-channels coated with the antigen-specific antibody. In addition, the presence of excess antibody in the cell sample during the run does not limit this methodology but can in fact mediate increased binding of the cellular antigens to the streptavidin matrix on the channel, thereby enhancing capture.

Example 3. Use of Multiple Antibodies Increases the Capture Rate of Target Cells It has traditionally been considered most efficient to pre-load an antibody onto the channel. However, the negative effects on cell capture of loading a channel with multiple antibodies have not been previously considered. An advantage of using a micro-channel coated with a general binding partner (e.g. antibody or protein) of an antigen-specific antibody is that multiple antibodies can be added to a cell suspension to pre-label cells without lessening the availability of any single antibody. Because multiple antigen sites on a cell are not mutually exclusive, when adding multiple antibodies to the cell suspension the capture efficiency on the channel is not diminished for any single antibody. By way of example, if the channel could accommodate 100 antibody sites and a mixture of 5 different antibodies were added to coat the channel, then each antibody would occupy ~20% of the channel space. Thus, the potential binding efficiency for each individual antibody is only 20% of what it would be if it covered the entire channel. Regardless of the number of antigens on the cell, the channel is inherently less efficient at capturing those cells with only 20% of that individual antibody. When the cell has a low number of target antigens, the efficacy in capturing these low antigen expressing cells can be amplified by the addition of the antibodies specific for other target antigen in the cell suspension prior to binding to the substrate or support of the micro-channel device. For example, if the same 5 antibodies are added to the cell suspension, then each antibody can maximally bind to all cognate cell surface antigens independently, without interference or reduction due to the presence of other antibodies bound to different epitopes on the cell. By derivatizing each of the five different antibodies with a common capture tag (e.g. biotin), a channel coated with a binding partner for the capture tag (e.g. streptavidin) can bind all 5 antibodies simultaneously to their respective antigens on the cell, thus producing an additive effect on cell capture.

Figure 7:
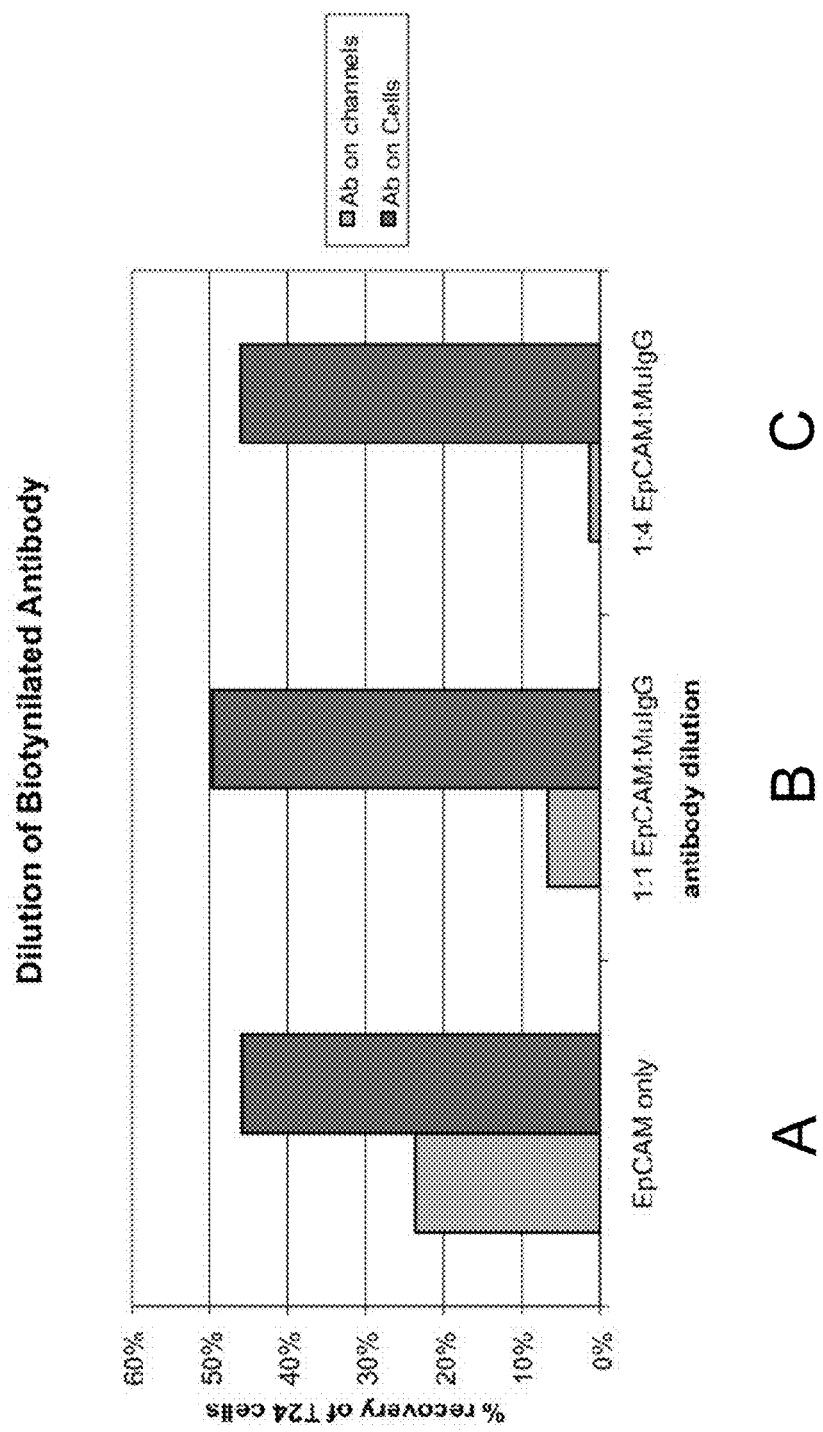
FIG. 7 is a graph showing the dilution of the EpCAM capture antibody that is coated onto the micro-channel compared to the capture of T24 cells as a function of the same dilution mixture used to pre-label cells prior to application onto the micro-channel.

FIG. 7 shows a reduction in the capture of T24 cells when the ratio of EpCAM antibody to murine IgG on the channel is lowered when the antibodies are first coated on the substrate/support of the micro-channel device. To determine the effect of EpCAM capture in the presence of additional biotinylated antibodies, the biotinylated EpCAM antibody was diluted with irrelevant biotinylated mouse IgG and the resulting mixture was used, either to coat the channel with antibody or added to the cell suspension prior to passage over the channel. FIG. 7 (sample A) shows that the percentage of T24 cell-capture is about twice as high when the cells were pre-labeled with biotinylated EpCAM antibody only. This observation is consistent with the results seen in FIG. 4. However, when the EpCAM antibody was diluted in a 1:1 ratio with an irrelevant antibody and used to either label the cells directly or to coat the channel, the channel recovery drops from 24% to 7%, while the recovery of pre-labeled cells is unaffected (FIG. 7, sample B). When the EpCAM was diluted in a 1:4, the recovery drops to 1% when the antibody mixture was first coated on the channel while the recovery is unchanged when the cells were pre-labeled with the antibody mixture prior to binding to the substrate or support of the microchannel device (FIG. 7, sample C). These results demonstrate that dilution of the EpCAM antibodies by additional antibodies do not interfere with the maximal binding of the EpCAM antibodies to the cells when the cells were prelabeled with the soluble antibodies, but that precoating of the channel with the diluted EpCAM antibodies shows a significant reduction in the capture of the low EpCAM expressing T24 cells. It is therefore evident that if the EpCAM antibody were mixed with 2 or 3 or 4 different antibodies for binding on the channel, even if the other antibodies were relevant to a surface antigen on the cell, the EpCAM antibody itself would be commensurately diminished in its binding effectiveness. Therefore, when adding multiple antibodies to the channel, the effect of each antibody cannot be expected to be additive. The overall effect on cell capture is unpredictable in this configuration since circulating tumor cell (CTC) antigen levels are variable. By definition the antibody in a mixture that might be directed towards the highest level antigen on the CTC will be diminished by the addition of antibodies to the lesser antigen levels on the CTC. If only one antibody in a mixture recognizes a dominant epitope on a particular CTC, then diluting with several other antibodies on the channel will adversely affect capture instead of enhancing it. By contrast, mixtures of soluble antibodies added to cells prior to passage over the channel are additive.

Figure 8:
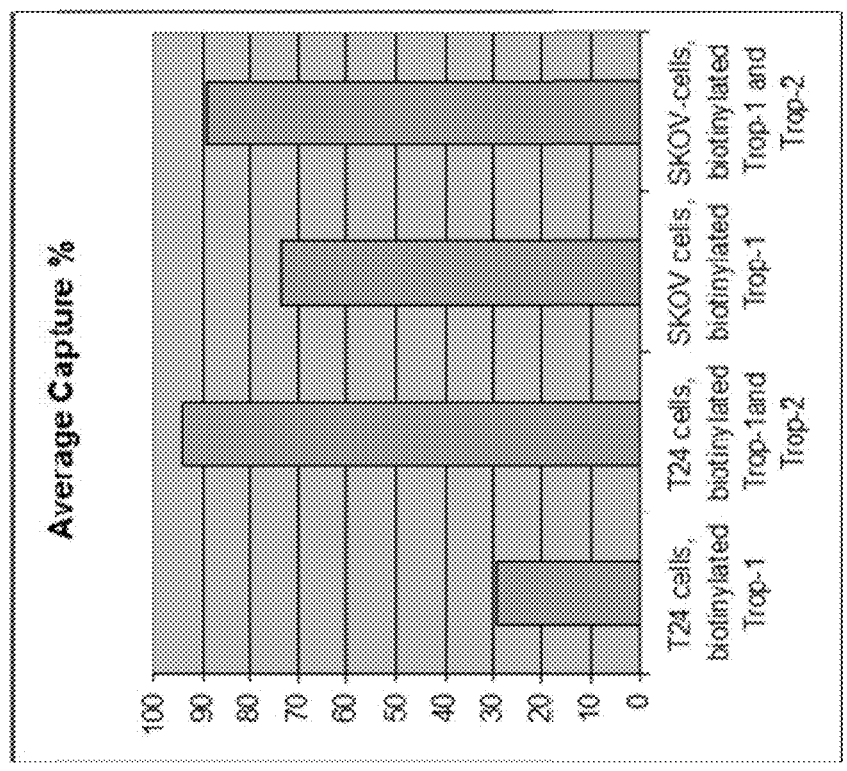
FIG. 8 is a graph depicting the percentage of T24 or SKOV cells captured on a streptavidin-coated micro-channel when pre-labeled with either biotinylated Trop-1 antibody alone or in combination with biotinylated Trop-2 antibody.

To demonstrate the additive effect of multiple antibodies on prelabeled cells prior to passage over the channel, two different antibodies to two different cell surface adhesion antigens, Trop-1 and Trop-2, were added to cell suspensions of either T24 bladder cells or SKOV ovarian cells. Each of the antibodies was biotinylated and cells were captured using a micro-channel device coated with streptavidin. When Trop-1 antibody was used to pre-load T24 cells, 29% of the cells are captured (FIG. 8). When Trop-2 antibody, which binds to a different antigen than Trop-1 antibody, was added in combination with the Trop-1 antibody, 94% of the cells are captured. A similar result is obtained with SKOV cells. A capture of 74% of the cells is observed with pre-labeling with Trop-1 antibody alone. However, a capture of 89% of the cells is observed when both Trop-1 and Trop-2 antibodies were added simultaneously (FIG. 8). The results show that addition of more than one antibody to more than one target site on the surface of the cell increases the effective number of channel-detectable molecules attached to the target cell and produces an additive effect on cell capture.

Figure 9:
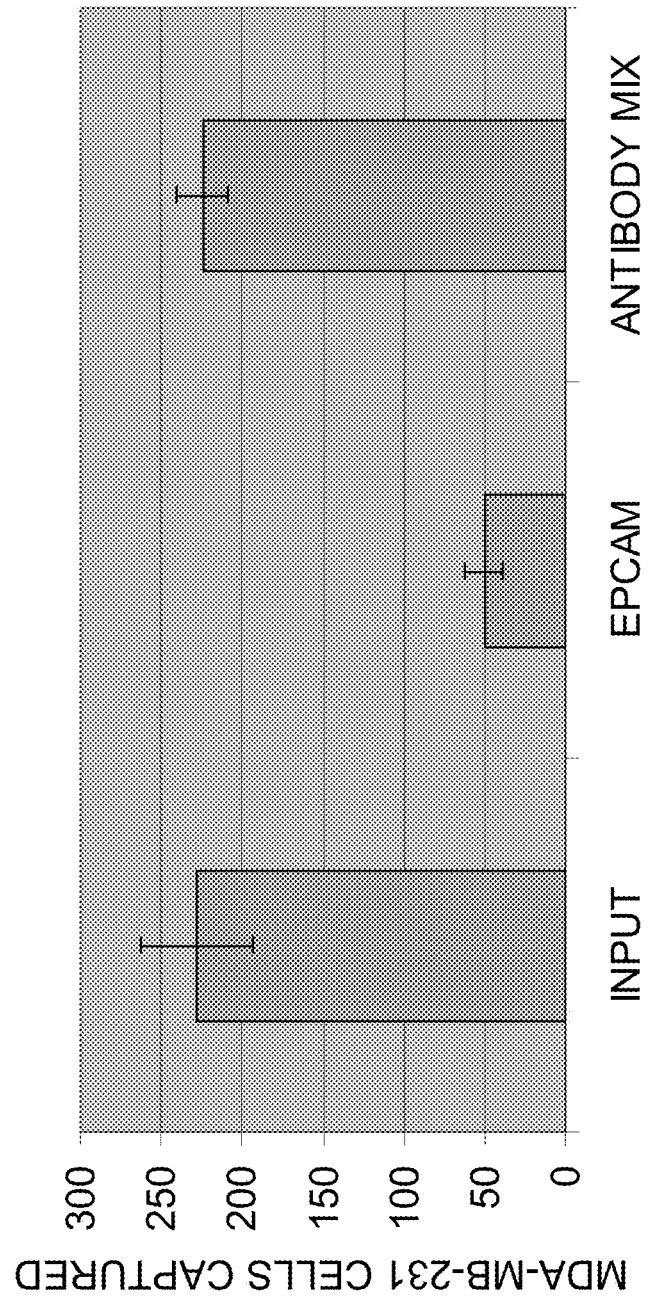
FIG. 9 is a graph depicting the capture of MDA-ND-231 cells on a streptavidin-coated micro-channel when pre-labeled with either biotinylated anti-EpCAM antibody alone or in combination with a mixture of biotinylated capture antibodies.

In FIG. 9 the same additive effect is observed using a different cell line and with a different antibody mixture. In this case the breast cancer cell line, MDA-MB-231, which has a low EpCAM expression was tested. In FIG. 9, the % capture with EpCAM antibody alone is low, but adding a mixture of 6 antibodies specific for the antigens: EpCAM, Trop-2, EGFR, MUC-1, CD318 and HER-2 improves capture to essentially 100%. FACS analysis of the MDA-MB-231 showed that this cell line has very low antigen expression of EpCAM, Trop-2, Her-2, and MUC-1 but higher expression of EGFR and CD318. Therefore, the antibodies to the higher expressing antigens were diluted 3-fold with antibodies to low expressing antigen. The diluted antibodies are still highly effective in capturing this low EpCAM-expressing cell line. This result is consistent with the results shown in FIG. 7 where antibodies were used to pre-label the cells.

Example 4. Secondary Antibody Labeling of Target Cells can Effect Capture in the Micro-Channel Device In some instances, a non-derivatized primary antibody may more efficiently bind to the antigen of interest or may be easier to employ. With some antibodies their activities are adversely affected by derivatization procedures which modify their surface amino acids. In cases, where one desires to use a non-derivatized primary antibody to bind to cellular antigens, a derivatized secondary antibody may be added to the cell suspension to form a complex with the primary antibody which is bound to the cellular target antigen. Thus, primary antibody mixtures, semi-purified or non-clonal hybridoma supernates can be added to the cell suspension and any antibodies that attach to antigens on the cell can be labeled by the addition of a derivatized (e.g. biotinylated) secondary antibody. Antibodies that do not bind to the cell are simply washed away.

Figure 10:
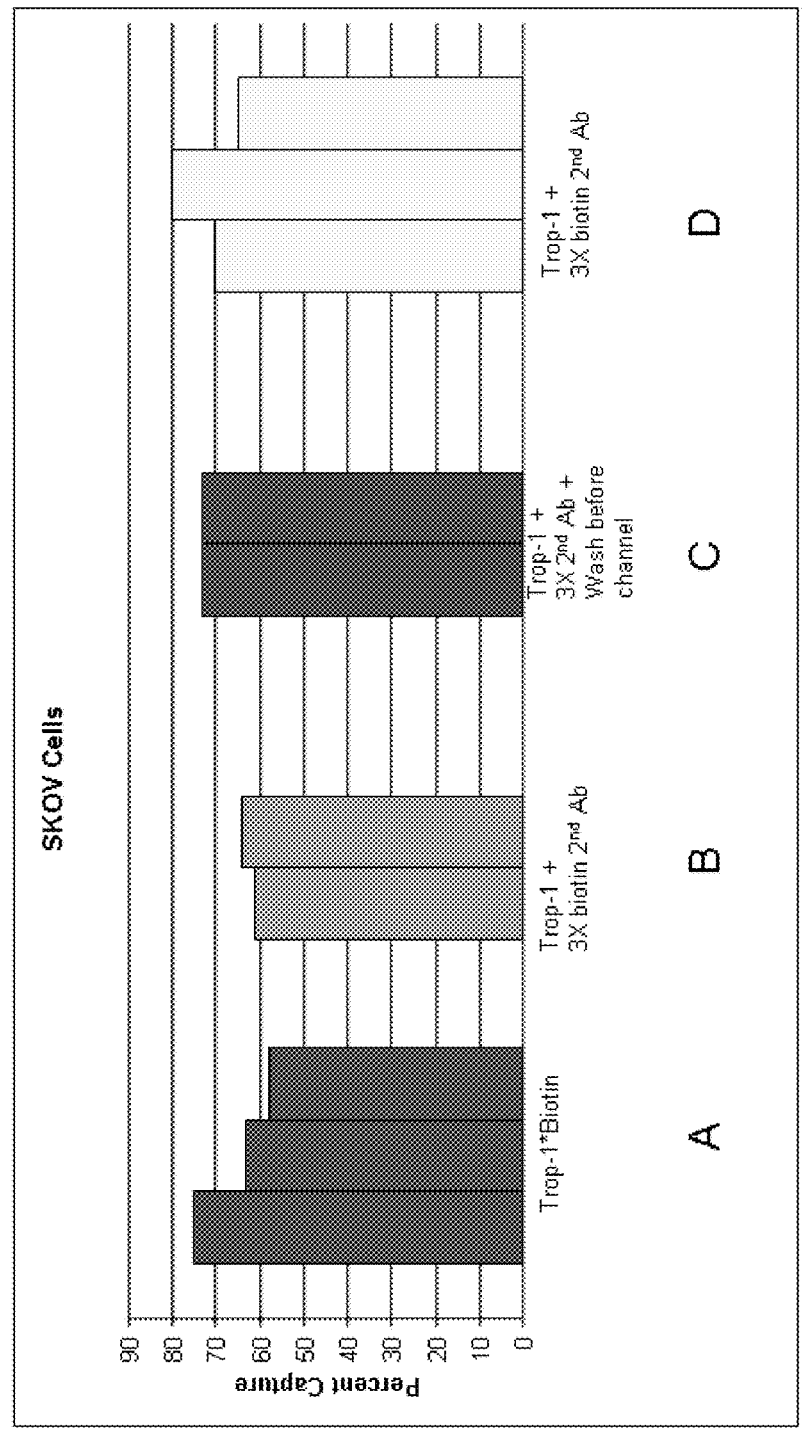
FIG. 10 is a graph depicting the percentage of captured SKOV cells on a streptavidin-coated micro-channel when pre-labeled with biotinylated primary antibody or a combination of non-biotinylated primary antibody and biotinylated secondary antibody.

To illustrate this approach, the cultured ovarian SKOV cell line was pre-labeled with either biotinylated Trop-1 antibody (Sample A in FIG. 10) or non-biotinylated Trop-1 plus a 3-fold molar excess of biotinylated anti-mouse secondary antibody. The primary antibody (Trop-1) concentration was 1 µg/mL and the cells were incubated for 30 mins. either with or without 3 µg/mL secondary antibody before cell capture and purification on a micro-channel device. The difference between samples B and D was that a longer biotin linker on the secondary antibody was used in sample D. In sample C, the cells were washed with PBS/BSA to remove excess primary and secondary antibody before applying the cells to the channel. In all samples, approximately 200 cells were suspended in 250 µL of PBS/BSA for application to the channel. As shown in FIG. 10, all samples have similar recovery. These results demonstrate that biotinylated secondary antibody can be used in combination with unlabeled primary antibody to pre-labeled cells for effective capture in a micro-channel device. The presence of some excess biotinylated secondary antibody did not adversely affect the capture percentage compared to direct pre-labeling with 1 µg of biotinylated Trop-1. Secondary antibodies may include intact IgG antibody, or antibody fragments such as Fab'2, Fab', Fab or engineered antibody fragments such as single chain Fab or single chain variable fragment.

Example 5. Stabilization of Captured Cells on Channel Surface

The process of capturing cells on a micro-channel device involves flow of cells suspended in a liquid. Therefore, the cells are subjected to sheer forces from the liquid flow that can also dislodge the cells from the channel after they are captured. This effect is more pronounced with cells that have lower surface antigen levels because there are relatively fewer attachment points between the cell and the specific cell surface antigens bound to the channel surface by the antibody. Therefore, it is advantageous to provide an additional external attachment of the cell to the channel surface by means of cross-linking reagents to better stabilize the attachment of the cell to the channel. Since the channel is typically coated with a binding protein (e.g. streptavidin or an antibody), a facile means of further anchoring the cell to the channel is through protein cross-linking reagents.

Reagents known in the art for this purpose can be homobifunctional NHS esters to crosslink amino groups on proteins. Another way of cross-linking is through the thiol or disulfide groups on the proteins with thiol reactive reagents, such as heterobifunctional molecules with a maleimide and an NHS ester. In addition, reagents such as EDC can be used to cross-link carboxyl and amino groups. The length of these cross-linkers can be varied by the use of polymeric regions between the two reactive groups, which typically take the form of chemical linkers such as polymeric ethylene glycol or simple carbon chains, but can also include sugars, amino acids or peptides, or oligonucleotides. Polymer chain lengths of from 5 to 50 nm are typical for this purpose but can be shorter or longer as needed. The common property of all of these protein cross-linking reagents is to covalently bind cellular proteins so as to anchor the cell to the surface of the channel by multiple covalent attachment points.

To examine whether externally added cross-linking reagents enhance retention of the captured cells on the coated micro-channels, cells were captured on coated micro-channels and subjected to high flow rates in the absence or presence of a protein cross-linker. Streptavidin-coated surfaces of micro-channels were prepared. The cultured T24 cell line, which is known to have a low expression level of surface EpCAM, was used as a model cell line. One µg/mL biotinylated anti-EpCAM antibody was incubated with the cells for 30 mins. at 4° C. and approximately 325 cells were suspended in 250 µL, of PBS/BSA buffer and passed in triplicates over coated micro-channels at 12 µL/min. The exact number of cells applied to the channel was determined microscopically by counting the cells in duplicate aliquots. After the cell suspension was passed through the channel, the channel containing bound cells was washed once with PBS/BSA and then a solution of homobifunctional NHS ester (bis N-succinimidyl-[pentaethylene glycol] ester) at 2 mM was passed over the channel and allowed to incubate for 20 mins. The control channel without NHS ester received only PBS/BSA solution. The cells were then washed with a 5% PEG solution in PBS for 2 mins. at various flow rates. The 5% PEG/PBS solution increases the solution viscosity and along with higher flow, provides more sheer force on the cells for purposes of this comparison. The cells captured in the channel were then stained with the nuclear staining dye, DAPI and counted.

Figure 11:
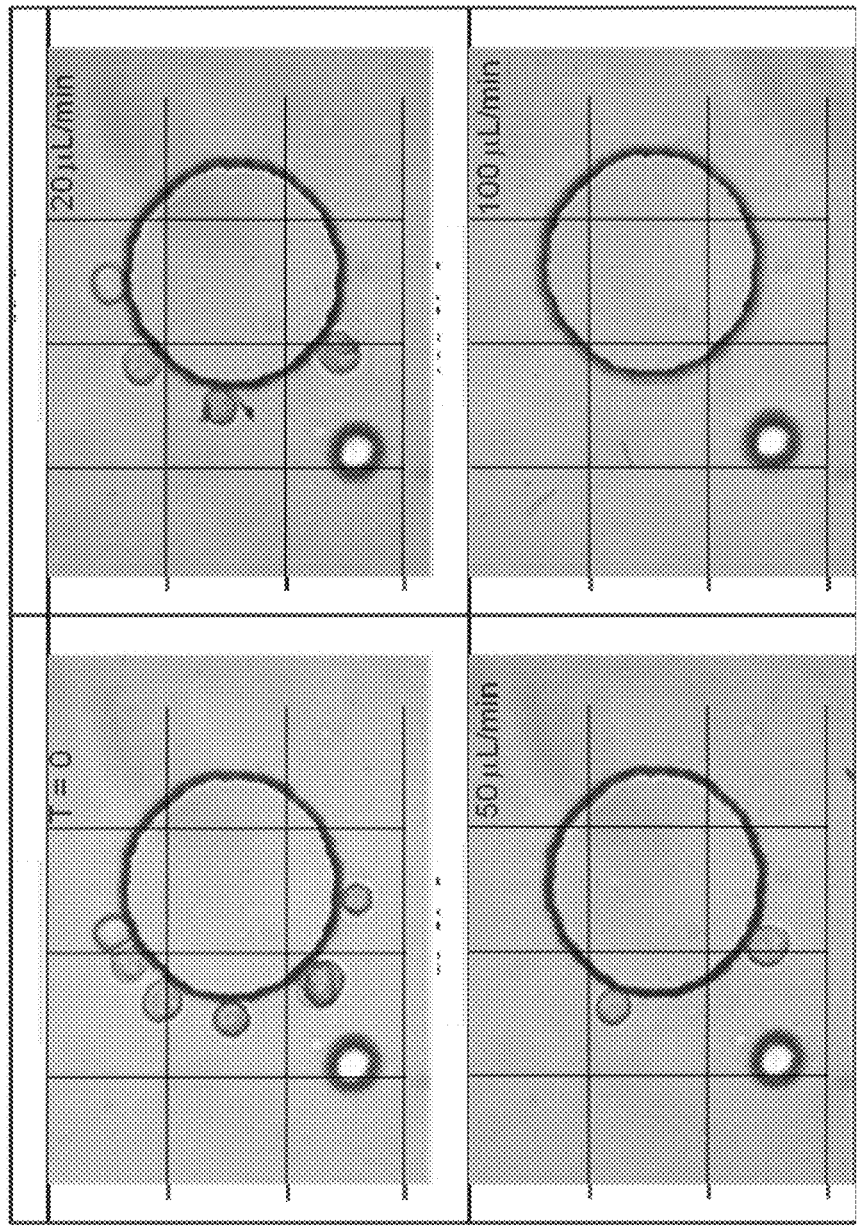
FIG. 11 shows a series of photomicrographs of cells captured in a coated micro-channel that were subsequently subjected to washes with a viscous solution at different flow rates (20, 50, and 100 µL/min).

FIG. 11 shows photomicrographs of captured cells subjected to different flow rates in the absence of protein cross-linker. Almost 50% of the cells are lost at a flow rate of 20 µL/min and all of the cells are lost at a flow rate of 100 µL/min.

Figure 12:
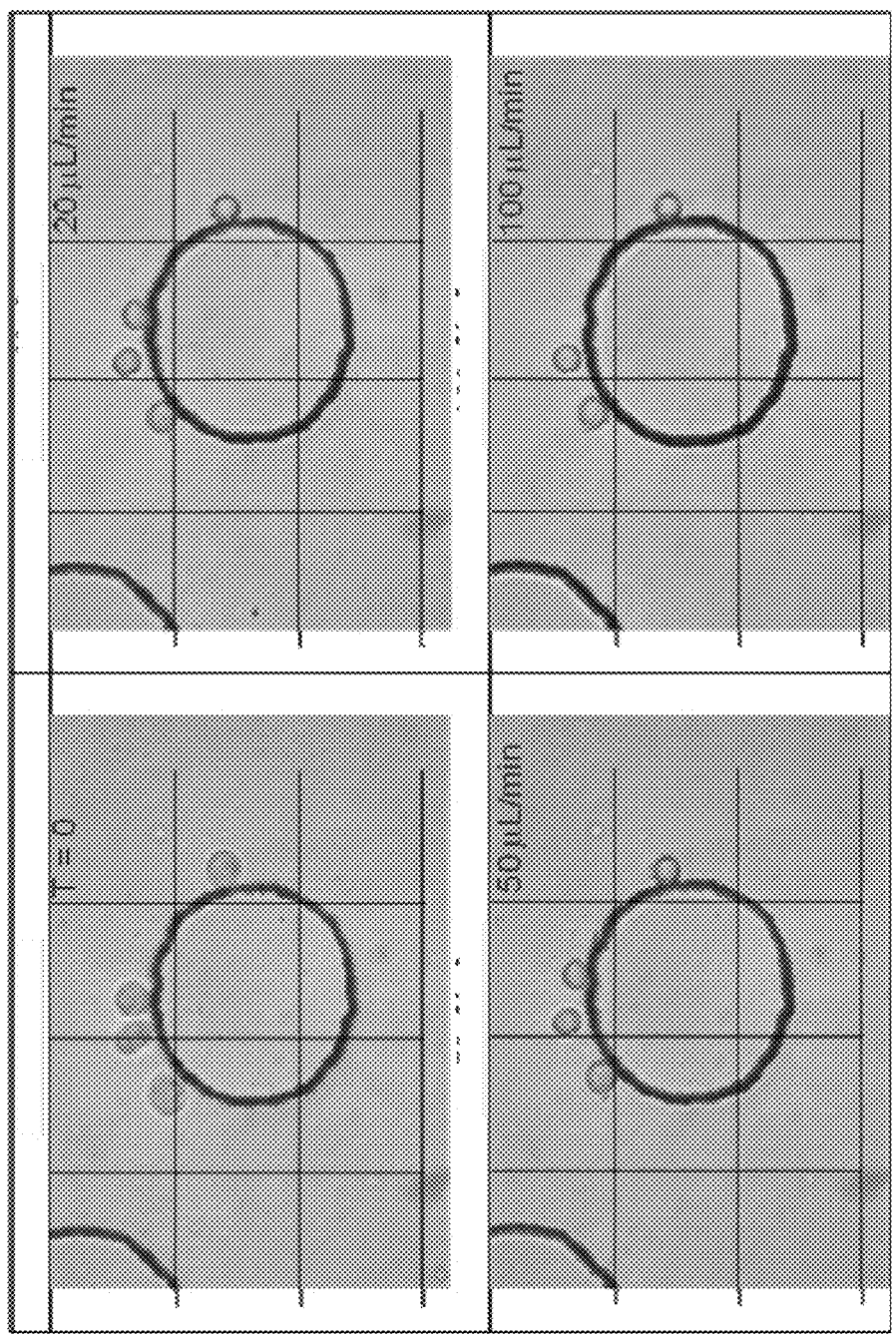
FIG. 12 shows a series of photomicrographs of cells captured in a coated micro-channel. The cells were exposed to a homobifunctional NHS protein cross-linking reagent prior to being subjected to washes with a viscous solution at different flow rates (20, 50, and 100 µL/min).

FIG. 12 shows photomicrographs of captured cells subjected to different flow rates after exposure to a NHS protein cross-linker. All cells are retained on the channel at flow rates of up to 50 µL/min and only one cell was lost at a flow rate of 100 µL/min.

Figure 13:
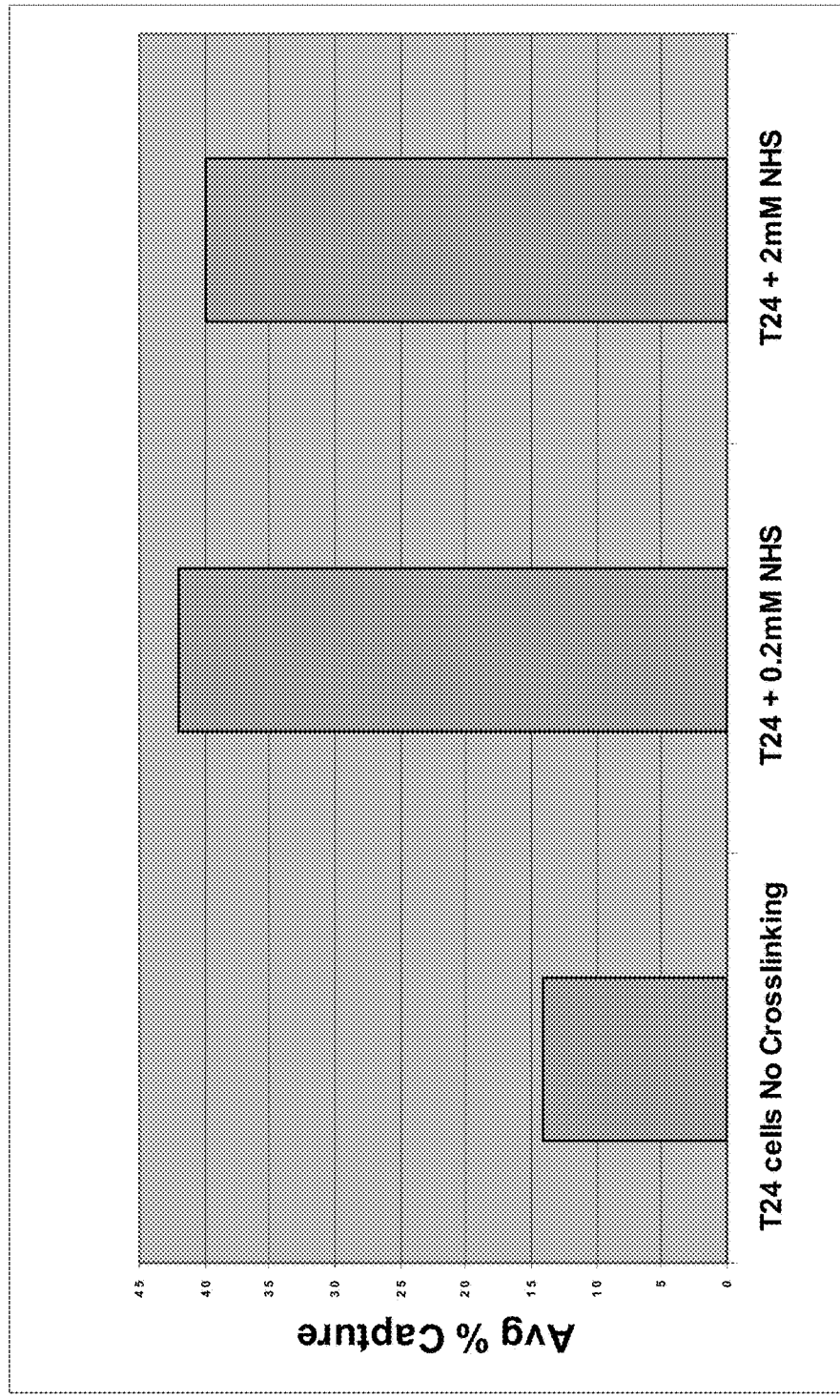
FIG. 13 is a graph showing the percentage of captured cells on a coated micro-channel in the absence or presence of a NHS protein cross-linking reagent.

A quantitative comparison of capture with and without cellular stabilization by protein cross-linking is shown in FIG. 13. As in previous experiments, approximately 200 T24 cells were applied to the micro-channel and after capture, the cells were washed with 5% PEG in PBS. FIG. 13 shows that less than 50% of the cells which not treated with crosslinking reagent are recovered compared to the percentage of cells recovered in channels treated with a crosslinker. Thus, the addition of protein cross-linking reagents significantly stabilizes cell attachment to the micro-channel. It should be noted that this result is independent of how the cells were captured on the micro-channel, whether by pre-loading antibody on the cells or on the channel, since the crosslinking agent stabilizes the cell on the micro-channel after the cells have been captured.

A second experiment similar to the above was employed to test for cell stability on the channel. After treatment of the cells with the protein crosslinker as above, the SKOV cells on the channel were subsequently stained with anti-cytokeratin (to visualize epithelial cells) and DAPI (to visualize cells with a nucleus). The difference in this experiment was that the tubing connected to the outlet was disconnected, a process that can cause transient but abrupt pressure pulses that can sheer and dislodge cells from the micro channel.

Table 1 shows the increasing numbers of cells lost when cells were not crosslinked to the channel were subjected to exogenous mechanical forces as a result of removing the outlet tubing. If cells were fixed to the channel with methanol treatment prior to removal of the tubing connections, there is no significant difference in cell recovery regardless of whether crosslinker was used (data not shown). However, methanol fixation (or any alcohol or acetone fixation) has several undesirable side-effects for the purposes of some subsequent cell analyses. Cells fixed with methanol are permeabilized due to disruption of the cell membrane and therefore cell surface studies cannot be distinguished from internal cell reactions. In addition, cells fixed with methanol become fused to the channel matrix making cell removal difficult and inefficient. Such cells can be subjected to extensive proteolysis to aid in cell removal, but cellular digestion has several undesirable side-effects for some types of subsequent cellular analysis. The procedure of crosslinking cells to the channel allows stabilized cells on the channel to be retained without alcohol fixation during normal channel operations and manipulations including higher flow rates, higher viscosity buffers and removal of channel connections.

TABLE 1

| Conditions | 2 mM Crosslinker + methanol | 2 mM Crosslinker No methanol | 0.2 mM Crosslinker No methanol | 0.07 mM Crosslinker No methanol |
| --- | --- | --- | --- | --- |
| % retained on channel | 100% (control) | 96% | 60% | 28% |

Example 6. Antibody Mixtures (Antibody Cocktail) Enhances Capture of Epithelial-Like and Mesenchymal-Like Cancer Cells Urothelial carcinoma (UC) cell lines have lower expression of EpCAM in more invasive tumor models. Such cells in circulation would be expected to limit the utility of EpCAM-based CTC capture. A cohort of 5 UC cell lines (UMUC3, UMUC5, UMUC9, T24, and KU7) were selected based on gene expression heat map analysis as being either more epithelial or more mesenchymal-like. In the latter case, these cells have undergone the epithelial to mesenchymal transition (EMT) which results in epithelial cells with mesenchymal expression and morphological characteristics. This EMT has been proposed as a mechanism by which epithelial cells can dissociate from the tumor and become more migratory and invasive in circulation.

These EMT cells were further tested by FACS for a variety of cell surface antigens. After identifying expression differences in these cell lines, an antibody mixture of EpCAM and 5 additional antibodies was selected to improve cell capture of all UC cell types. We subsequently compared cell capture rates using microfluidic channels with the antibody mixture compared to EpCAM alone. Cells were also immunostained with cytokeratin and vimentin antibodies to help further distinguish cells having epithelial or mesenchymal-like expression characteristics, respectively.

Figure 14:
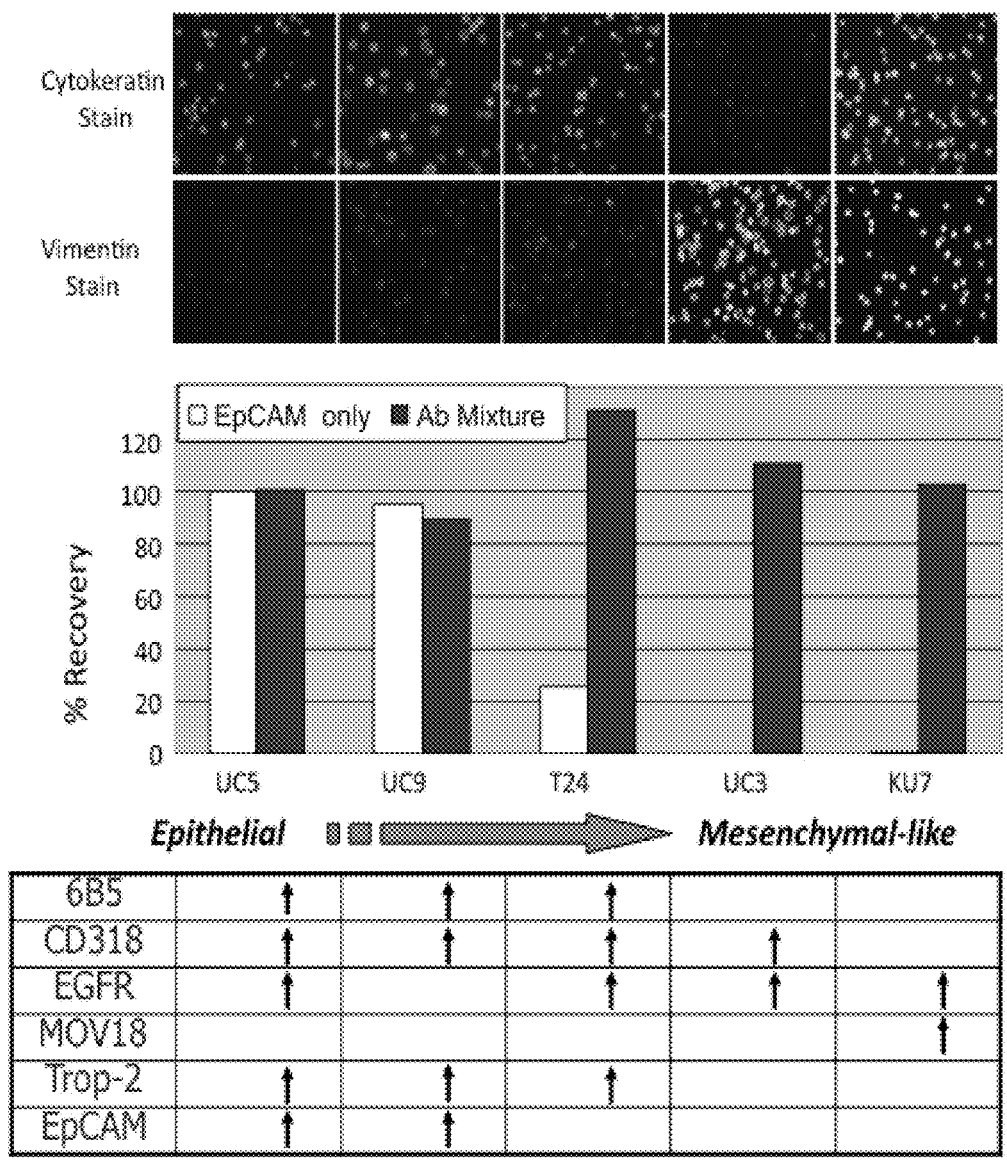
FIG. 14 is a graph showing the percentage of captured bladder cancer cells on a coated micro-channel when using EpCAM only as the capture antibody compared to using a mixture of antibodies. The graph also shows the staining of the cell types with anti-cytokeratin and anti-vimentin antibodies.

FIG. 14 shows the staining of the 5 UC cells lines with vimentin and cytokeration. Among the 5 UC cell lines, 2 (UC3 and KU7) stained with vimentin and had minimal to no expression of EpCAM. While these cells lines retained some degree of cytokeratin staining, one cell line stained only with vimentin (FIG. 14). The remaining 3 lines (UC5, UC9 and T24) stained only for cytokeratin and had significant EpCAM expression. Those cell lines with no EpCAM expression (UC3 and KU7) had no cell recovery when EpCAM alone was utilized as the capture antibody. However, when the antibody mixture, comprising 6b5, CD318, EGFR, MOV18, Trop-2 and EpCam) was used, all 5-cell lines achieved nearly 100% cell capture rates. In the case of KU7, the most mesenchymal-like of this group of cell types, the folate binding receptor (MOV18) was unique and not expressed in the other cell lines.

The results show that the use of a mixture of antibodies allows capture of both bladder epithelial cells and bladder epithelial cells that had undergone EMT. The study shows that the use of antibody mixtures provides a dramatic improvement over cell recovery compared to the use of a single antibody alone, such as EpCAM alone. Because of the heterogeneity of tumor cell types expected in circulation, such an approach is expected to significantly improve the capture and isolation of CTCs from patient samples.

Example 7 Capture of Low-Antigen Expressing Cells on a Micro-Channel Device Increases with Antibody Mixture or Cocktails Common detection methods are needed when cocktails of antibodies are used to simultaneously bind to several different cancer cell types. While cytokeratin stain works well for epithelial cells, some epithelial cells have lost cytokeratin expression as described in Example 6. With other cells types, such as stem cells, there is no specific method for staining these cells that does not have significant crossreactivity to other blood cell types which may be non-specifically bound to the channel. However, high levels of biotinylated primary or secondary antibodies on the surface of the cells are common to all cells captured specifically by the avidin on the microchannel. The benefit of using cocktails of biotin-conjugated antibodies is the additive effect in increasing surface biotins on target cells, which is useful for increasing the capture of low antigen-expressing cells or cells expressing variable levels of one or more antigens in a heterogenous cell population, such as those found in tumor patients. See FIGS. 8, 9, and 13.

The unexpected additional advantage of using multiple antibodies in a cocktail is that this provides a common detection method for a heterogenous population of cells that have variable level of antigen expression An example of this is shown in FIG. 15.

Figure 15A:
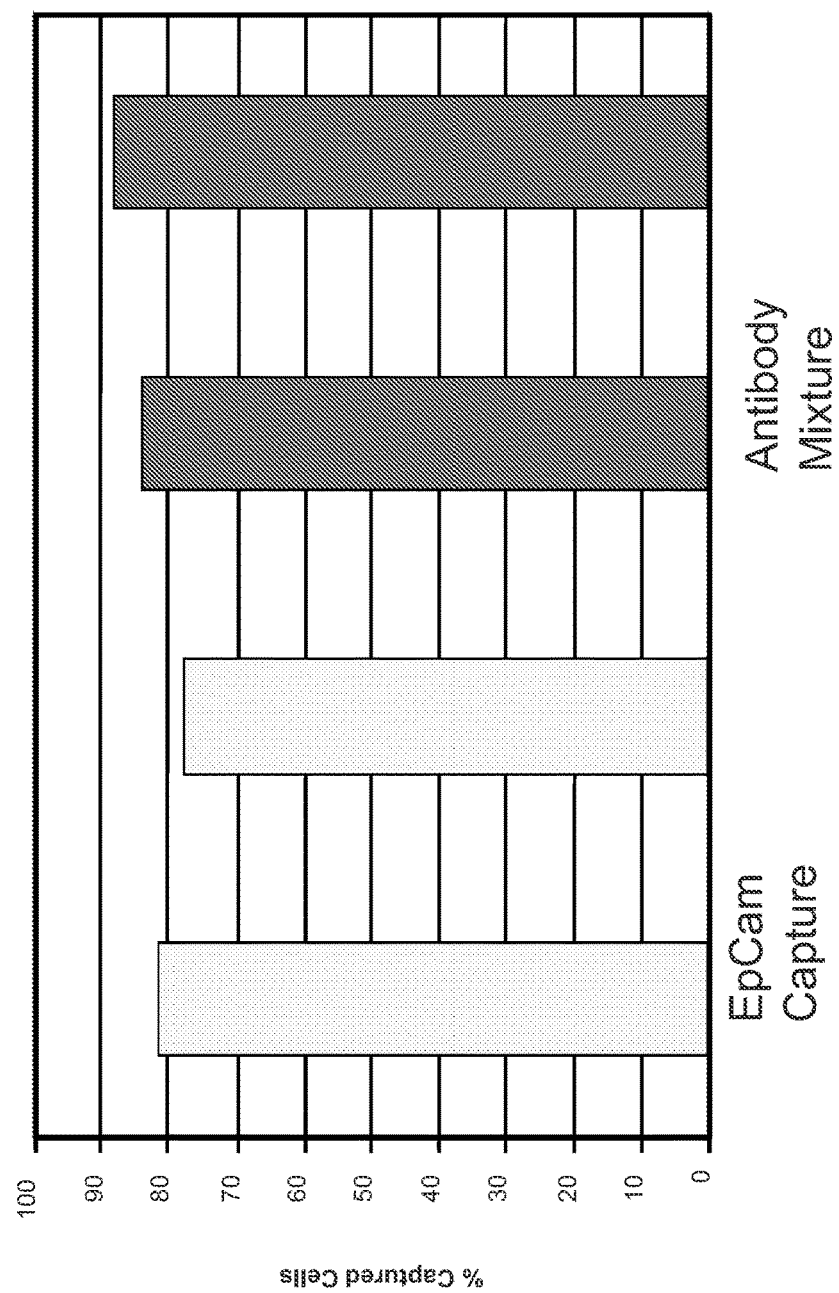
FIG. 15A is a graph showing the capture of SKOV cells by EpCAM antibody compared to capture by an antibody mixture.

FIG. 15A shows the percentage capture of SKOV cells, which is known to express a high level of EpCam antigen (approximately 40-70,000 EpCam antigens per cell (apc)), with EpCam alone or with a mixture of antibodies specific for other surface antigens expressed by the cells, including EpCAM, Trop-2, EGFR, MUC-1, CD318 and HER-2. The results show that there is no significant improvement in the percent number of SKOV cells captured with EpCam antibody alone or a mixture of antibodies specific for other antigens in addition to EpCam.

Figure 15B:
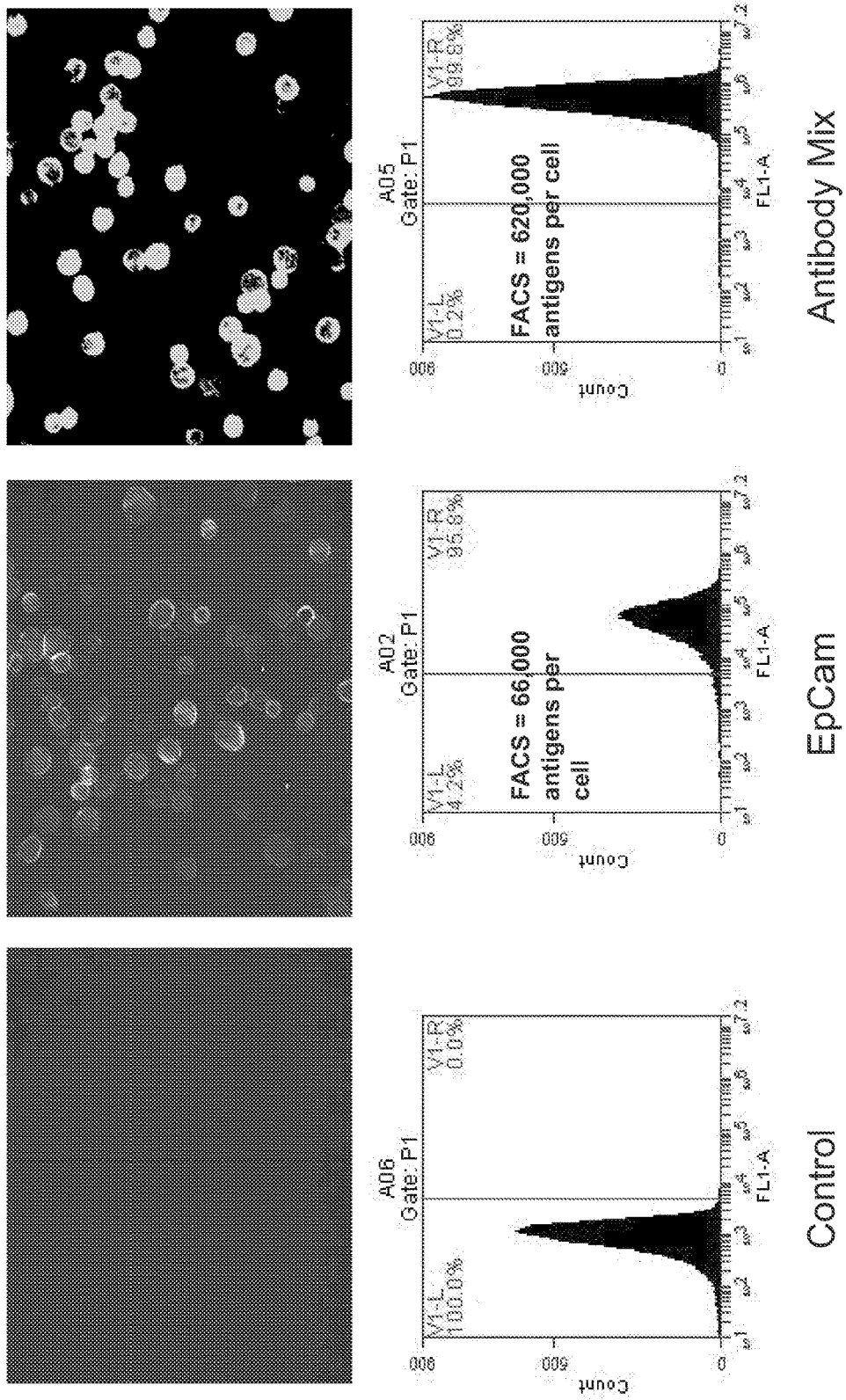
FIG. 15B shows the staining of SKOV cells after incubation with EpCAM antibody or antibody mixture and detected with fluorescently labeled secondary anti-mouse antibody. FACS analysis of the same cells shows the number of surface antigens labeled with labeled secondary anti-mouse antibody.

In contrast, FIG. 15B shows the fluorescence staining intensity of the same SKOV cells by FACS and on slides. These cells stain with very different intensities depending on whether they have been pre-mixed with EpCam alone (~66,000 surface antigens) or with an antibody mixture which are directed against Her-2, CD24, CD44, combined surface antigen level of ~600,000 antigens as determined by the FACS analysis. Fluorescently labeled anti-mouse antibody was used to label the primary antibodies. While there was minimal increase in the capture of these antibody cocktail-incubated SKOV cells using biotinylated secondary antibody as shown in FIG. 15A, using fluorescently labeled secondary antibody in FIG. 15B shows that the staining intensity is significantly higher when using the antibody mixture. In a similar manner, this differential would be obtained if cells were reacted with primary antibody, followed by biotinylated secondary antibody and fluorescently labeled biotin-reactive avidin. Thus there is an significant advantage in using antibody cocktail mixtures even when additional antibodies are not necessary for capture of the cells. In the case of a low EpCam-expressing cells, the capture using EpCam antibody alone is reduced (FIGS. 4-6, 14), but is significantly increased when using an antibody cocktail. In this case the staining intensity based on the number of antibodies bound to the surface of the cells would also be increased. Therefore the use of fluorescently-labeled molecules that target the multiple antibodies used to better capture the cells has the universal advantage of better detection of those same cells. The use of antibody cocktails has the unique advantage in allowing detection of cells for which there may not be a known specific marker for detection such as cytokeratin in epithelial cells, or where the cytokeratin has been lost as shown in FIG. 14. The multiple antibodies used in a mixture for better capture of cells with variable expression of surface markers can still be targeted for fluorescence labeling based solely on their increased levels of bound antibodies from the antibody cocktail.

Figure 16:
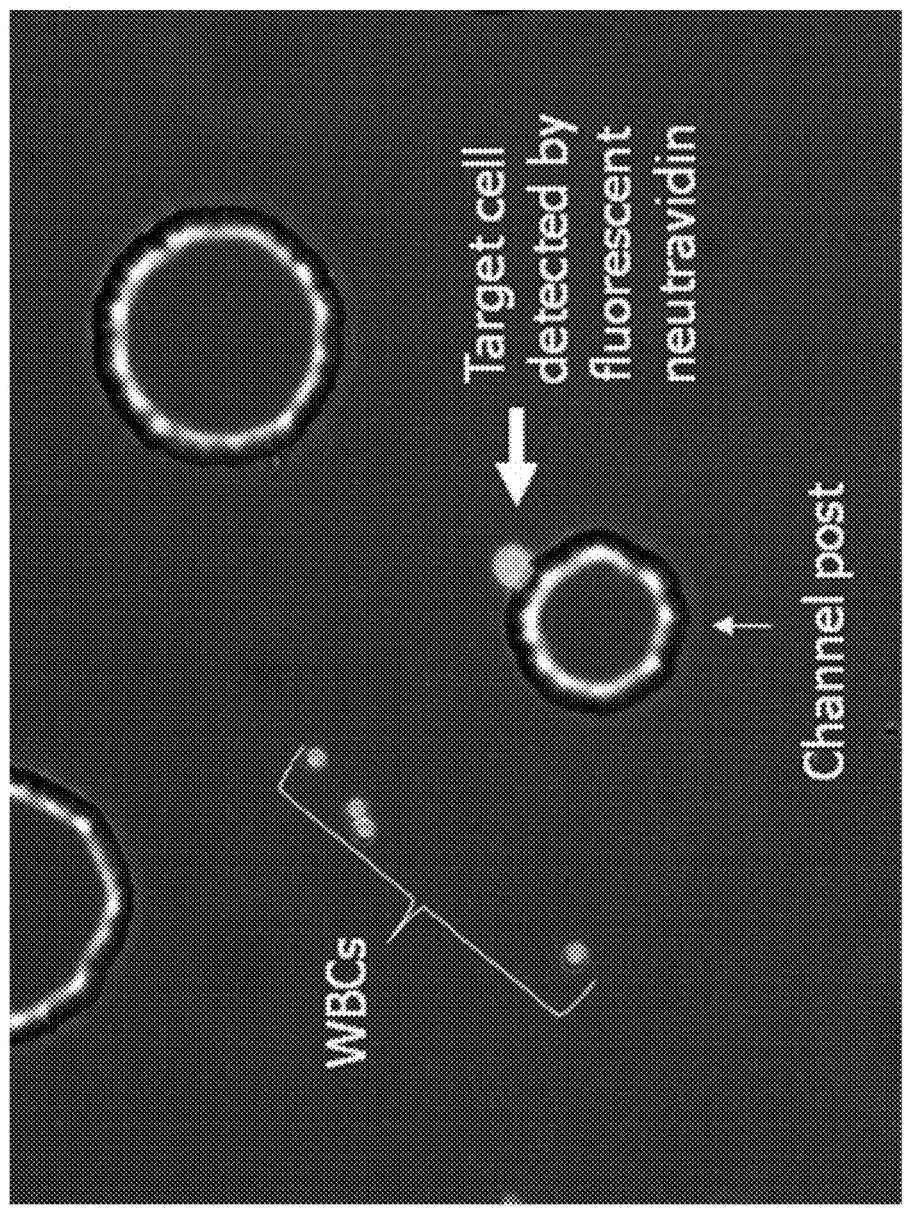
FIG. 16 is an image of SKOV cells spiked into blood and captured on a microchannel using a primary antibody mixture and biotinylated secondary anti-mouse antibody. Cells were stained on the channel with fluorescently labeled neutravidin which tightly binds biotin. Image shows SKOV cell stained green with NeutrAvidin and nearby white blood cells that did not stain with neutravidin but stained only with DAPI to detect the nucleus.

FIG. 16 shows the additive effect of multiple antibodies in a cocktail, which contain antibodies specific for the SKOV target cells and which are shown to associate minimally to the non-specific cells present in a blood sample, when the blood sample was spiked with SKOV target cells. The antibody cocktail contained antibodies directed against CD340, EGFR, CD318, Muc-1, Trop-2, EpCam, Mov-18, MSC, c-met and N-Cadherin. Although some of the non-specific cells in the sample may have adsorbed some of the biotinylated antibodies (either primary or secondary) added to the samples, the level of antibodies adsorbed is far too low to be visualized using fluorescently-labeled neutravidin. The differential staining between specific target cells and non-specific cells favors the visualization of the target cells which have higher numbers of biotinylated antibodies from the antibody mixture bound or captured by the target cells. FIGS. 15 and 16 demonstrate that addition of multiple antibodies in a cocktail provides a common and universal method of detecting rare cell types that express low levels of antigens on the microchannel. Thus, the antibody cocktail used to enhance and thereby increase capture of circulating tumor cells that are highly variable in heterogenous cell population in a sample, also enhance detection of any of the captured cells.

Example 8: The Micro-Channel Device is Superior at Capturing Cells from Biological Samples that are Present in Low Cell Numbers In FIG. 17, blood samples were spiked with a variable number of SKBr3 cells, a cell line expressing high levels of EpCAM, ranging from about 10-250 cells per 10 mL blood sample. EpCAM antibodies were added to the spiked blood sample and the EpCAM Ab-bound cells were captured on a micro-channel device using the method described in Example 1.

Figure 17:
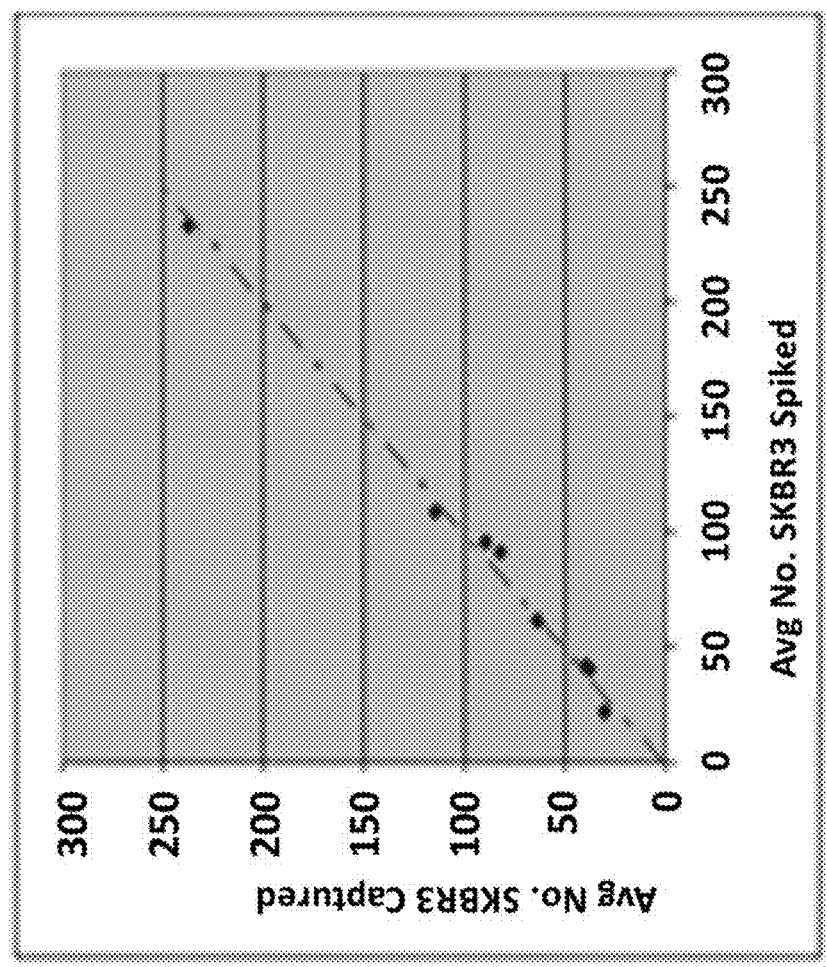
FIG. 17 shows the recovery of SKBr3 in a blood sample spiked with varying numbers of SKBr3 cells. The results show that the percent capture is independent of the cell input.

The results in FIG. 17 shows that approximately a 100% of the SKBr3 cells were recovered from the spiked samples. The data shows that the percent capture of cells by the micro-channel device is independent of the cell input.

Example 9: Antibody Cocktail is Superior at Capturing Circulating Tumor Cell (CTC) from Patient Blood Samples Using Micro-Channel Device Table 2 shows the results of circulating tumor cells (CTCs) captured on a micro-channel device from 10 mL blood samples from patients diagnosed with prostate, lung, pancreatic, renal cell, colorectal, breast and ovarian cancers. The blood samples were pre-labeled with a cocktail of soluble antibodies containing antibodies directed against CD340, EGFR, CD318, Muc-1, Trop-2, EpCam, Mov-18, and MSC, or a anti-EpCAM only. Cells were identified by staining with fluorescently labeled anti-cytokeratin.

TABLE 2

| Sample No.* | Anti-EpCAM only | MAb Cocktail |
|---|---|---|
| 1 (16283 - Prostate) | 0 | 2 |
| 2 (16302 - Prostate) | 0 | 3 |
| 3 (16318 - Prostate) | 95 | 77 |
| 4 (16291 - Ovarian) | 1 | 1 |
| 5 (16278 - Colo/rectal) | 0 | 4 |
| 6 (16288 - Lung) | 0 | 5 |
| 7 (16297 - Breast) | 1 | 3 |
| 8 (16296 - Breast) | 0 | 3 |

*Samples from prostate, lung, pancreatic, renal cell, colorectal, breast and ovarian cancers.

TABLE 2 shows that the blood samples pre-labeled with a soluble antibody cocktail is superior at capturing CTCs compared to samples pre-labeled with a single type of antibody alone.

Example 10: The Micro-Channel Device is Superior at Capturing CTCs when Blood Samples Obtained from Breast Cancer Patients that are Pre-Labeled with a Soluble Antibody Cocktail on a Micro-Channel Device as Compared to Capture of CTCs Using a Ferro-Magnetic Label Antibody Blood samples were pre-incubated with anti-EpCAM antibody for capture on a micro-channel device or pre-incubated with antibodies that are joined to microscopic iron particles (immunoferromagnetic Abs) and captured using CellSearch® (VERIDEX, LLC). The captured cells were stained for CK, CD45 markers and DAPI, a nuclei stain. The cells that were stained in-situ with $CK^+/CD45^-/DAPI^+$ were counted.

TABLE 3

| Sample ID | Total #CTCs by CEE ($CK^+/CD45^-/DAPI^+$)* | Veridex |
|---|---|---|
| 16163 | 0 | 0 |
| 16170 | 0 | 0 |
| 16171 | 60 (34) | 54 |
| 16172 | 5 | 0 |
| 16173 | 0 | 1 |
| 16176 | 549 (325) | 1267 |
| 16187 | 104 (37) | 54 |
| 16196 | 0 | 0 |
| 16198 | 87 (27) | 32 |
| 16202 | 5 | 8 |
| 16203 | 2008 | 923 |
| 16205 | 78 | 51 |

*No Significant difference by Two Tailed t-test (P = 0.715)
Total CTC counts indicated in bold include robust, apoptotic and micronuclei; whereas numbers in parenthesis indicate robust CTCs.

TABLE 3 shows that the total number of CTCs captured on the micro-channel device that are $CK^+/CD45^-/DAPI^+$ are consistently more than the CTCs captured by the VERIDEX systems, indicating that the invention provides for superior capturing of CTCs.

Example 11: Post-Capture Molecular Analysis of Captured Cells Increases Identification of CTC as Cancer Cells in Stage III and IV Breast Cancer Patients Circulating tumor cells (CTCs) were captured from blood samples of Stage IV (TABLE 4) and III (TABLE 5) breast cancer patients. The CTCs were pre-labeled with an antibody cocktail, containing antibodies to CD340, EGFR, CD318, Muc-1, Trop-2, EpCam, Mov-18, and MSC, and were released from the micro-channel device. The captured cells were analyzed by fluorescent in-situ hybridization (FISH) for aneuploidy in chromosome 8 and 17, and amplification of the breast cancer marker, Her2 (TABLE 4) These cells were never released from the microchannel and all FISH is performed in the channel with cells relocated following enumeration for FISH analysis. The total number of CTCs found positive for aneuploidy were compared to the total number of cells stained positive for CK marker.

TABLE 4

| Sample # | #CTCs ($CK^+$) | #Aneuploid cells (Chrom 17 & 8) | Her2/chromosome 17 Ratio |
|---|---|---|---|
| 1 | 3 | 7 (6 $CK^-$) | 1.05 |
| 2 | 1 | 1 ($CK^-$) | 1.0 |
| 3 | 0 | 3 ($CK^-$) | 1.0 |
| 4 | 0 | 3 ($CK^-$) | 1.0 |
| 5 | 0 | 4 ($CK^-$) | 1.0 |
| 6 | 2 | 13 ($CK^-/CK^+$) | Mixed |
| 7 | 1 | 1 ($CK^-$) | 1.0 |
| 8 | 1 | 7 ($CK^-$) | 0.95 |
| 9 | 510 | 7 ($CK^+$) | 1.0 |
| 10 | 16 | 16 ($CK^-/CK^+$) | >6 |
| 11 | 1 | 2 ($CK^-$) | 1.0 |
| 12 | 0 | 4 ($CK^-$) | 1 |
| 13 | 0 | 2 ($CK^-$) | 1 |
| 14 | 0 | 14 ($CK^-$) | 1 |
| 15 | 0 | 1 ($CK^-$) | 1.5 |

TABLE 4-continued

| Sample # | #CTCs (CK+) | #Aneuploid cells (Chrom 17 & 8) | Her2/chromosome 17 Ratio |
|---|---|---|---|
| 16 | 0 | 24 (CK−) | 1.98 |
| 17 | 3 | 9 (CK−) | 5.714 |

TABLE 4 shows that post-capture molecular analyses of CTCs from stage IV breast cancer patients for aneuploidy and Her2 amplification status are superior in detecting breast cancer cells from the captured CTCs compared to CK staining.

In TABLE 5, captured CTCs from the blood samples of patients diagnosed with Stage III cancer were analyzed for aneuploidy in chromosome 8, 11 and 17. The total number of CTCs found positive for aneuploidy were compared to the total number of cells stained positive for CK marker. The details of aneuploidy on chromosomes 8, 11 and 17 are shown.

TABLE 5

| Sample ID | #CTCS (CK+) | #Aneuploid cells | Aneuploid Details (Chromosomes 8, 11 and 17) |
|---|---|---|---|
| 16610 | 0 | 93 | 4- Monosomy 8; 6- Monosomy 11; 83- Monosomy 17 |
| 16620 | 0 | 55 | 26- Monosomy 8; 11- Monosomy 11; 16- Monosomy 17; 2- complex aneuploidy |
| 16621 | 0 | 54 | 8- Monosomy 8; 22- Monosomy 11; 23- Monosomy 17; 1 - Trisomy 17 |
| 16631 | 0 | 169 | 11- Monosomy 8; 11- Monosomy 11; 265- Monosomy 17; 3- complex monosomies |
| 16632 | 0 | 61 | 9- Monosomy 8; 10- Monosomy 11; 40- Monosomy 17; 2- complex Monosomy 8, 11, 17 |
| 16633 | 0 | 6 | 2- Monosomy 8; 1- Monosomy 11; 3- Monosomy 17 |
| 16686 | 0 | 55 | 13- Monosomy 8; 13- Monosomy 11; 21 Monosomy 17; 1- Trisomy 8; 1- Trisomy 11; 1- Trisomy 17 |
| 16687 | 0 | 686 | 12- Monosomy 8; 82- Monosomy 11; 582- Monosomy 17 |
| 16720 | 0 | 56 | 8- Monosomy 8; 23- Monosomy 11; 25- Monosomy 17 |
| 16747 | 0 | 58 | 11- Monosomy 8; 19- Monosomy 11; 26- Monosomy 17; 1- Tetrapolid 8; 1- Trisomy 17 |
| 16754 | 0 | 531 | 21- Monosomy 8; 123- Monosomy 11; 380- Monosomy 17; 7- complex aneuploidy |

Although none of the CTCs captured from the blood of Stage III breast cancer patients were stained positive for CK marker (CK+), post-capture analyses for aneuploidy at chromosome 8, 11 and 17, showed that a large number of the captured CTCs are aneuploid cells indicating that these CTCs are tumor cells. In-situ hybridization study using FISH to detect Her2 (table 4) amplification and aneuploidy (Table 4 an 5) confirms that captured CTCs which are CK− are breast cancer cells. The results in Tables 4 and 5 show that post-capture molecular analyses, such as amplification of the Her2 marker and detection of aneuploidy of the captured cells released from the micro-channel device, positively identify cancer cells in CK− cells from Stage III and IV cancer patients. This study shows that CTCs captured within the micro-channel device provide a robust method for identifying cancer cells which would otherwise be left undetected.

Example 12: Post-Capture Molecular Analysis of Captured Cells Increases Identification of CTC as Cancer Cells in Bladder Cancer Patients Circulating tumor cells (CTCs) were captured from blood samples of bladder cancer patients. The CTCs were pre-labeled with an antibody cocktail, containing antibodies to CD340, EGFR, CD318, Muc-1, Trop-2, EpCam, Mov-18, MSC, c-met and N-Cadherin. Captured cells were analyzed directly within the micro-channel device by fluorescent in-situ hybridization for aneuploidy in chromosome 3, 7 and 17, and compared to staining for CK marker on the captured CTCs.

TABLE 6

| Sample ID | #CTCS (CK+) | #Aneuploid cells | Aneuploid Details (Chromosomes 3, 7 and 17) |
|---|---|---|---|
| 16660 | 0 | 17 | 12-Trisomy 3; 1- Monosomy 3; 2- Monosomy 7; 2- Monosomy 17 |
| 16664 | 0 | 13 | 1- Trisomy 3; 2- Monosomy 3; 4- Monosomy 7; 6- Monosomy 17 |
| 16708 | 0 | 27 | 14- Trisomy 3; 2- Monosomy 3; 8- Monosomy 17; 2- Monosomy 7; 1- Tetraploid 3 |
| 16714 | 0 | 78 | 7- Monosomy 3; 3- Monosomy 7; 68- Monosomy 17 |
| 16719 | 0 | 8 | 2- Monosomy 3; 1- Monosomy 7; 5- Monosomy 17 |
| 16729 | 0 | 29 | 2- Monosomy 3; 5- Monosomy 7; 10- Monosomy 17; 12- Trisomy 3 |
| 16746 | 0 | 20 | 1- Monosomy 17; 13- Trisomy 3; 1- Trisomy 7; 2- Trisomy 17; 1- Monosomy 3; 2- Monosomy 7 |
| 16762 | 0 | 18 | 2- Monosomy 3; 12- Monosomy 17; 3- Trisomy 3; 1-complex aneuploid (triploid for 3, 7, 17) |
| 16761 | 0 | 46 | 1- Monosomy 3; 5-0 Monosomy 7; 8- Monosomy 17; 26- Trisomy 3; 2- Trisomy 17; 4- Tetraploid 3 |

Table 6 shows that the many of the captured cells from samples obtained from patients with bladder cancer which are stained negative for CK ($2^{nd}$ column) are aneuploid cells (monosomy, trisomy and/or tetraploid at chromosome 3, 7 and 17). The results in Table 6 show that the method is capable of identifying CTCs from blood obtained from different cancer types.

The results from these experiments show that the ability to identify aneuploidy and expression of specific markers in CTCs captured on a micro-channel device provide a means for predicting and managing diseases, such as cancer during the early stages of tumorigenesis or late stages of tumorigenesis where tumor cells have metastasized and escaped into the circulation. In addition, the method described is also applicable for monitoring treatment efficacy or failure.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. A device for detecting a target cell in a sample, comprising
    a surface and a pre-loading mixture,
    wherein the pre-loading mixture comprises a pre-loading reagent consisting essentially of a first binding entity that is an antibody or antibody cocktail capable of specifically binding to a target entity on the target cell in the preloading mixture
    and a third binding entity that is a secondary antibody conjugated to a detectable entity, wherein the third binding entity specifically binds to the first binding entity of the pre-loading reagent in the pre-loading mixture, and
    wherein the surface is coated with a second binding entity that specifically binds to the third binding entity in the pre-loading mixture, thereby binding indirectly to the first binding entity of the pre-loading reagent via the third binding entity, wherein the second binding entity is not an antibody.

2. The device of claim 1, wherein the surface comprises a population of posts distributed in an irregular pattern.

3. The device of claim 1, wherein the surface is a microchannel.

4. The device of claim 1, wherein the first binding entity comprises a binding entity mixture having at least a first antibody and a second antibody, and wherein the first antibody is capable of specifically binding to a first epitope of the target entity and the second antibody is capable of specifically binding to a second epitope of the target entity.

5. The device of claim 1, wherein the first binding entity:
    a) includes an antibody that specifically binds to an epithelial cell surface marker, or
    b) is an epithelial cell adhesion molecule (EpCAM) antibody.

6. The device of claim 1, wherein the target cell is a rare cell present in a biological sample at a ratio of 1 out of $10^{10}$ cells, 1 out of $5 \times 10^7$, or 1 out of $10^4$ cells.

7. The device of claim 6, wherein the biological sample is a physiological fluid or tissue selected from the group consisting of blood, plasma, bone marrow, serum, semen, vaginal secretions, urine, saliva, amniotic fluid, cerebral spinal fluid, synovial fluid, lung lavages, fine needle aspirates (FNA) and biopsy tissue sample.

8. The device of claim 1, wherein the target cell is a circulating tumor cell (CTC) and/or a cancer cell selected from the group consisting of a breast cancer cell, a prostate cancer cell, a colorectal cancer cell, a lung cancer cell, a pancreatic cancer cell, a ovarian cancer cell, a bladder cancer cell, a endometrial cancer cell, a cervical cancer cell, a liver cancer cell, a renal cancer cell, a thyroid cancer cell, a bone cancer cell, a lymphoma cancer cell, a melanoma cancer cell, and a non-melanoma cancer cell.

9. The device of claim 1, wherein the target cell is a melanoma cancer cell and wherein the first binding entity is an antibody that specifically binds to melanocyte differentiation antigens, oncofetal antigens, tumor specific antigens, serological identification of antigens by recombinant expression cloning (SEREX) antigens or a combination thereof.

10. The device of claim 9, wherein:
    a) the melanocyte differentiation antigens comprise tyrosinase, gp75, gp100, MelanA/MART1 or Trp2;
    b) the oncofetal antigens comprise melanoma antigen gene (MAGE)-A1, MAGE-A4, B melanoma antigen gene (BAGE), G melanoma antigen gene (GAGE) or New York esophageal squamous cell carcinoma 1 (NY-ESO1); and/or
    c) the tumor-specific antigens comprise cyclin-dependent kinase 4 (CDK4) and β-catenin.

11. The device of claim 1, wherein the target cell is selected from the group consisting of:
    a) a breast cancer cell and the first binding entity is an antibody that specifically binds to epithelial cell adhesion molecule (EpCAM), mucin 1 (MUC-1), epidermal growth factor receptor (EGFR), prostate specific membrane antigen (PSMA), prostate specific antigen (PSA), tumor associated calcium signal transducer 2 (TACSTD2), prostate stem cell antigen (PSCA), prostate cell surface antigen (PCSA), CD318, CD104, or N-cadherin, or the first binding entity is an antibody cocktail specifically binding a combination thereof;
    b) a prostate cancer cell and the first binding entity is an antibody that specifically binds to EpCAM, MUC-1, EGFR, PSMA, PSA, TACSTD2, PSCA, PCSA, CD318, CD104, or N-cadherin, or the first binding entity is an antibody cocktail specifically binding a combination thereof,
    c) a colorectal cancer cell and the first binding entity is an antibody that specifically binds to EpCAM, CD66c, CD66e, carcinoembryonic antigen (CEA), TACSTD2, cytokeratin 20 (CK20), CD104, MUC-1, CD318, or N-cadherin, or the first binding entity is an antibody cocktail specifically binding a combination thereof;
    d) a lung cancer cell and the first binding entity is an antibody that specifically binds to CK18, CK19, TACSTD2, CD318, CD104, CEA, EGFR, or EpCAM, or the first binding entity is an antibody cocktail specifically binding a combination thereof;
    e) a pancreatic cancer cell and the first binding entity is an antibody that specifically binds to MUC-1, CEA, TACSTD2, CD104, CD318, N-cadherin, MUC-1, or EpCAM, or the first binding entity is an antibody cocktail specifically binding a combination thereof;
    f) an ovarian cancer cell and the first binding entity is an antibody that specifically binds to MUC-1, TACSTD2, CEA, CD318, CD104, N-cadherin, or EpCAM, or the first binding entity is an antibody cocktail specifically binding a combination thereof;

g) an endothelial bladder cancer cell and the first binding entity is an antibody that specifically binds to CD34, CD146, CD62, CD105, CD106, vascular endothelial growth factor (VEGF) receptor, or MUC-1, or the first binding entity is an antibody cocktail specifically binding a combination thereof;

h) an epithelial bladder cancer cell and the first binding entity is an antibody that specifically binds to TAC-STD2, EpCAM, CD318, EGFR, 6B5, N-cadherin or folate binding receptor, or the first binding entity is an antibody cocktail that specifically binds a combination thereof, i) a cancer stem cell and the first binding entity is an antibody that specifically binds to CD133, CD135, CD117, or CD34, or the first binding entity is an antibody cocktail that specifically binds a combination thereof;

j) a circulating cancer cell that expresses mesenchymal antigens and the first binding entity is an antibody that specifically binds to fibroblast growth factor receptor 1 (FGFR1), FGFR4, EGFR, folate binding receptor, N-cadherin or mesenchymal stem cell antigen (MSC), and the first binding entity is an antibody that specifically binds a combination thereof; or k) a circulating cancer cell that expresses angiogenesis surface antigens and the first binding entity is an antibody that specifically binds to a VEGF receptor.

12. The device of claim 1, wherein the first binding entity is a primary antibody, the third binding entity is a biotinylated secondary antibody that specifically binds to the first binding entity and the second binding entity is avidin, streptavidin, or neutravidin.

* * * * *